US012587381B2

(12) United States Patent
Kimmel et al.

(10) Patent No.:    US 12,587,381 B2
(45) Date of Patent:    Mar. 24, 2026

(54) METHOD AND SYSTEM FOR MONITORING AND CONTROLLING HIGH RISK SUBSTANCES

(71) Applicants: Joshua M. Kimmel, Knoxville, TN (US); Kenneth M. Greenwood, Davenport, FL (US)

(72) Inventors: Joshua M. Kimmel, Knoxville, TN (US); Kenneth M. Greenwood, Davenport, FL (US)

(73) Assignee: Revolution Medicines, Inc, Knoxville, TN (US)

( * ) Notice: Subject to any disclaimer, the term of this patent is extended or adjusted under 35 U.S.C. 154(b) by 0 days.

(21) Appl. No.: 17/428,931

(22) PCT Filed: Feb. 5, 2020

(86) PCT No.: PCT/US2020/016776
§ 371 (c)(1),
(2) Date: Aug. 5, 2021

(87) PCT Pub. No.: WO2020/163465
PCT Pub. Date: Aug. 13, 2020

(65) Prior Publication Data
US 2022/0131699 A1    Apr. 28, 2022

(51) Int. Cl.
*H04L 9/32* (2006.01)
*A61M 5/172* (2006.01)
*H04L 9/00* (2022.01)
*H04L 9/08* (2006.01)

(52) U.S. Cl.
CPC ........... *H04L 9/3231* (2013.01); *A61M 5/172* (2013.01); *H04L 9/0825* (2013.01); *A61M 2205/3592* (2013.01); *A61M 2205/6009* (2013.01); *A61M 2205/609* (2013.01); *H04L 9/50* (2022.05); *H04L 2209/46* (2013.01)

(58) Field of Classification Search
CPC ....... H04L 9/3231; H04L 9/0825; H04L 9/50; H04L 2209/46; A61M 5/172; A61M 5/50; A61M 2205/3592; A61M 2205/6009; A61M 2205/609
See application file for complete search history.

(56) References Cited

U.S. PATENT DOCUMENTS

| | | | | |
|---|---|---|---|---|
| 10,545,132 | B2 * | 1/2020 | Guthrie | G16H 20/17 |
| 11,017,892 | B1 * | 5/2021 | Knas | A61B 5/117 |
| 11,083,850 | B2 † | 8/2021 | Hatamian | |
| 11,090,449 | B2 † | 8/2021 | Hatamian | |
| 2008/0300902 | A1 * | 12/2008 | Smith | G16H 20/10 705/1.1 |
| 2018/0028406 | A1 * | 2/2018 | Patton | A61J 7/0069 |
| 2018/0302222 | A1 * | 10/2018 | Agrawal | H04L 9/3213 |

(Continued)

*Primary Examiner* — Farid Homayounmehr
*Assistant Examiner* — Brian William Avery
(74) *Attorney, Agent, or Firm* — Jurgen Klaus Vollrath

(57) ABSTRACT

In a system and method for globally tracking, monitoring, and authorizing the dispensing of valuable and high-risk products such as drugs, secure delivery devices are needed, coupled to a blockchain serving as a distributed database forming a ledger of the journey of the devices and the dispensing of the product, to allow changes to the ledger to be agreed upon by participants in the blockchain through a consensus mechanism.

17 Claims, 15 Drawing Sheets

(56)         References Cited

U.S. PATENT DOCUMENTS

| | | | |
|---|---|---|---|
| 2019/0065970 A1* | 2/2019 | Bonutti | G06T 7/0012 |
| 2019/0180291 A1* | 6/2019 | Schmeling | G16H 20/10 |
| 2019/0240430 A1* | 8/2019 | Jackson | A61M 15/0065 |
| 2019/0341142 A1* | 11/2019 | Nag | H04L 63/1425 |
| 2020/0061301 A1* | 2/2020 | Hatamian | A61M 5/31546 |
| 2020/0162266 A1* | 5/2020 | Miller | H04L 9/3236 |
| 2020/0294642 A1* | 9/2020 | Bostic | G16H 50/20 |
| 2021/0366589 A1† | 11/2021 | Hatamian | |
| 2022/0165384 A1* | 5/2022 | Jibaja | G16H 10/60 |

* cited by examiner
† cited by third party

METHOD AND SYSTEM FOR MONITORING AND CONTROLLING HIGH RISK SUBSTANCES

FIELD OF THE INVENTION

The invention relates to a method and system for tracking and monitoring the use of prescription medicines such as opioids, as well as other high value or high-risk substances and materials.

BACKGROUND OF THE INVENTION

Opioid abuse and addiction is one of the most severe health crises in the US and worldwide. In 2013 the economic cost due to opioids was estimated to be $78B for the US alone. In the same year 15281 deaths were ascribed to overdosing on commonly prescribed opioids, 2.1 million people misused commonly prescribe opioids for the first time, and 2 million had prescription opioid use disorders. Some 93 million adults are prescribed opioids annually for analgesic purposes, and half a million adults annually enter into medication-assisted therapy. In 2016 the economic burden to the US due to the opioid epidemic hit $95B.

The FDA has expressed a commitment to addressing this national crisis, with a focus on encouraging medical product innovation to prevent new cases of opioid abuse and addiction, and to treat those addicted. As part of important efforts to address the epidemic of opioid misuse and abuse, the FDA launched an innovation challenge on May 31, 2018, to spur the development of medical devices, including diagnostic tests and digital health technologies to help combat the opioid crisis and achieve the goal of preventing and treating opioid use disorder.

Today, if a doctor prescribes opioids in pill or capsule form, or a hospital patient is prescribed a drip with an opioid solution that is either pre-mixed or added to a drip by a nurse or other hospital staff, there is little in the way of safeguards to prevent that prescribed pain killer or a portion thereof from being stolen, diverted, or abused. Also, there is the issue of validating the movement and administration of drugs and other high value substances, without requiring the intervention of human arbiters. Currently, there are a limited number of solutions that allow for the tracking of commodities and materials. To address the validation challenge, Blockchain platforms have been developed to provide a distributed ledger of various types of transactions, such as the transfer of cryptocurrencies. However, there is a need for managing not only the transfer of digital currencies or digital records, but also physical materials and devices.

More generally, there is therefore a need to build in protections to avoid loss and abuse of drugs and other high value substances. Specifically, there is a need to avoid unauthorized people from taking or diverting the drug and also to avoid patients from abusing the prescribed dosage through over-use or by selling it to third parties.

SUMMARY OF THE INVENTION

The Summary of the Invention and Detailed Description provided herein describe certain embodiments of the present application in order to provide a basic understanding of the invention. They are not intended to define the scope of the invention or identify key or critical elements.

Furthermore, systems, computer-implemented methods, processors, and computer program products are described that facilitate synchronization of processes for distributed processing of blockchain transactions.

The present application deals with the tracking, management and transfer of physical materials. There are a wide variety of products and materials that are transported on a daily basis between different locations, or that accompany users, and which would benefit from being traced, monitored aid managed.

According to one aspect of the present application, there is provided a method, system and computer program product for tracking the location and monitoring the use of devices, controlling access to the devices, and gathering information relating to one or more of: the location of the devices, materials conveyed and delivered or dispensed by the devices, user information, and sensor information gathered by the devices, and using such information to control the devices, materials conveyed and delivered or dispensed by the devices, and communicate and interface with the users, for example by generating reports.

For purposes of this application, the term "devices" is used to cover any device capable of housing a material or substance for dispensing. Thus, it includes individual user-devices for housing, conveying and dispensing high risk or high value products like drugs. It also includes larger inventory storage devices that may serve to replenish user-devices.

In order to avoid valuable and high-risk products (also referred to herein as substances or materials) such as drugs, e.g., opioids, from being abused, stolen, diverted, redirected or otherwise lost or end up in the wrong hands, it is necessary to start by packaging the product differently.

Thus, one aspect of the present invention includes providing a secure housing or a secure delivery device (which for purposes of this application will also be referred to as a material delivery device, or substance-dispensing device or simply as a device). The second aspect of the present invention, as mentioned above, is a system and method for globally tracking the device, and either monitor or authorize any removal or dispensing of product from the device.

For purposes of this application, the term system includes one or more delivery devices, a networking infrastructure and associated software.

For purposes of this application the term client will mean a generic peer device and/or the software on that device, which includes delivery devices and filling stations for those delivery devices, and their associated software.

For purposes of this application the term user will mean an operator of a device, or component of a device, or software forming part of the system, as well as an initiator or recipient of any data analysis or report. The user may comprise a human, non-human, or hybrid user. The term non-human user includes any type of non-human user, such as a physical or virtual machine with autonomous or non-autonomous identity, including programs or intelligence, e.g., artificial intelligence systems.

Although this document primarily describes a method, device and system for monitoring, tracking and controlling the use of drugs, the invention is not so limited. As discussed above it includes a method and system for monitoring and tracking inventory, and subsequently monitoring and tracking substances, and controlling their use, which when used with various dispensing mechanisms suitable for the substance, can track the substance, and monitor and control the dispensing of the substance. This may include a biometrically-controlled method and system.

In this document the term patient is used synonymously with the term user. While the term patient is typically used for medical use cases and scenarios, it is not intended to be so limited. The terms user and patient are used herein to include any user who could operate any component of this invention in a generalized inventory-control scenario.

For purposes of this application the term substance will mean any substance or material in general for consumption or use by the user, including, but not limited to any or all medicinal substances such as drugs, and any or all non-medicinal substances such as perfume, venom, biological agents, or radioactive material, which may be in liquid, powder or solid form.

For purposes of this application the term dose includes any measured amount of substance or material dispensed by the dispensing device, including medical and non-medical uses, such as the issuing of substance from inventory.

To avoid abuse or diversion at every step of the journey of the substance and the devices it is desirable to perform the tracking and monitoring, and/or the authorization from time of packaging through every step of the journey, all the way to the return of the device and any remaining amount of substance to an authorized dispensing or recycling entity.

Thus, according to the invention there is provided a global, hack-resistant monitoring, tracking, authentication, and authorization system, configured to receive data from one or more product delivery devices and operable to perform for each device, at least one of tracking the location of the device, monitoring of the product (e.g., the amount of the substance in a device or dispensed by a device), authentication of a user, and authorizing the dispensing of product.

In the preferred embodiment, the devices may form part of one or more private or public peer-to-peer networks, although any network type is possible, such as client-server, by-proxy, or other type of network, wherein each device is configured to (a) gather and submit information, and (b) process information. As such each device may be considered as part of a network defining an internet of things (IoT), while also defining a peer, a client or in general, a node in any network type.

One implementation of the system employs a blockchain storage design. This has the benefits of providing an immutable ledger of transaction or activity data that is associated with the devices, the materials carried by the devices, and the users who use the devices, by providing a platform with multiple participants in a network, each having access to some or all of the data, which may be time-stamped, and can continuously be updated.

Blockchain is essentially a multi-node database whereby data is redundantly stored on multiple nodes and nodes co-operate to maintain and agree upon the integrity of the totality of the data in its redundant form by forming a chain of blocks of data that define the historical changes to that data. Changes to the chain need to be agreed upon by a set of participants in the blockchain, and is therefore also referred to as a consensus mechanism. Current common consensus mechanisms are Proof of Work or Proof of Stake (discussed further below). In addition, by making use of a hash algorithm and timestamp, it ensures that data on a blockchain is immutable, verifiable and traceable.

A variety of Blockchain platforms have evolved over the last few years. For instance, the Bitcoin blockchain works on a proof of work (PoW) paradigm, i.e. all processors compete to perform a hash function. Thus, each participant or processor works on the same problem, which amounts to a huge waste of resources. Once a processor has obtained a set of records to sign it generates a header and thus creates a block. Processors on the blockchain then add a 4-byte field (called a nonce) containing a random number to the block and generates a hash from the totality. If the hash does not meet target criteria set by the network (e.g., with 5 leading zeros), the processor at that node iterates by changing the nonce to a new random number and re-running the hashing algorithm until the node obtains a hash value which meets the defined target criteria. The result is that the fastest processors win more frequently and get compensated more often in bitcoin for signing a block. The other processors then validate the hash generated by the first processor, and if the validation passes, they all add the block to their copy of the chain.

The EOS blockchain works on proof of stake (PoS) rather than proof of work—i.e. the computer system with the most stake in the network (a combination of resources and longevity and perhaps other factors) more often are assigned the duty of signing a block—the others on the chain simply verify the correctness of the answer.

According to one aspect of the invention there is provided a blockchain platform comprising, multiple devices which act as nodes in a network, each including one or more node processors, sensors, communications means, and data storage for holding at least in part the blockchain, and which blockchain can be considered a specialized form of database for storing at least one of: master data, transaction data, configuration data, and system data, such as status of the device, status of material contained within the device, information gathered by the sensors, information processed by the node processor(s), device and material schedule, and configuration information, history of this information and similar information from other nodes on the network.

The communications means may include a transmitter and a receiver.

A central server may contain a copy of the blockchain wherein the central server is configured to perform at least one of processing and analyzing of information received from the devices, monitoring the network and its nodes, and disseminating data to the network and its nodes.

The central server may communicate with the devices to control the devices. The central server may also provide information to users of the devices and may analyze information received from the devices, and generate reports, for example for third parties, such as health or governmental agencies.

The node devices may contain or communicate with one or more dispensing components for carrying and dispensing liquid or solid material. One or more aspects of the blockchain includes disseminating configuration information to the node devices, or storing transactions, wherein the transactions are comprised of information about user interaction with the devices, including one or more of user-identifying information, amount of product dispensed, time of dispensing, and geographic location of the device. The node devices may validate new transactions and other types of record sets—a record set being a set of one or more records—from other node devices in order to achieve consensus and add new blocks to the chain. Each device may therefore process and transmit local blocks of information to other devices and may receive new blocks and records from other devices and may validate those blocks.

In this context the blockchain serves as a distributed database forming a ledger of the journey of a device and the use of the product that is housed by the device. In a blockchain environment, identification and authentication may be performed on the network, and changes to the ledger may be agreed upon by critical participants in the blockchain. As mentioned above, this is achieved through a consensus mechanism such as Proof of Work or Proof of Stake. It may also be implemented using a proprietary algorithm such as Distributed Statistical Recognition. In addition, the use of a hash algorithm and timestamp ensures that data on a blockchain is immutable, verifiable and traceable.

The device may be remotely controlled, e.g. to allow dispensing of a dose (or in the case of a solid substance or material, to allow release of all or part of that material), by sending confirmation information to the device via a network, e.g., a client-server network, or using a peer-to-peer network, which, as discussed above, may include a blockchain platform for secure transmission of information, and with the ability of validating the identify of a user. The transmission of information to the device to control the delivery of substance may include consensus-based user authentication. Thus, authentication may include both local authentication e.g., using a biometric sensor on the device or linked to the device, as well as distributed user authentication, including at least one of an asymmetric key encryption scheme with a public key to encrypt and a private key to decrypt the information, and consensus-based authentication involving consensus amongst a group of users. The private key may, for example, be stored on a separate personal device associated with the user, such as a smart phone, which may be configured to communicate with the delivery device to decrypt incoming information.

According to one aspect of the invention there is provided a method and system for reducing drug abuse, such as opioid abuse, and for addressing the problem of opioid addiction by providing a global data gathering, and overview system of what is happening to the drug from day to day by gathering data from hack-resistant prescription-drug delivery devices, which data includes at least one of, dispensing of drugs, and requests for dispensing of drugs from the devices. It may also include the gathering of data on the locations of the devices.

For purposes of this application, drug abuse incudes not only overdosing or re-distribution by the patients but also drug theft, drug dilution, diverting or redirecting of drugs, and over-prescribing of drugs by entities that dispense or deliver prescription drugs to users, e.g., physicians, nurses, pharmacists, etc.

The overview system may include one or more of: physically tracking the locations of dispensing devices, and performing at least one of, monitoring and controlling the delivery of dosages. Thus, the system includes not only the gathering and analyzing of data from devices but also the ability to communicate information back to the devices, e.g., dosage adjustment or dosage authorization information. In a system where dosages are pre-defined for a user, dosages may be subsequently adjusted for that user based on user feedback or data gathered during monitoring of the usage of that user's device or various biological and psychological metrics which measure and record the patient's physiological and psychological reactions to a dose. The monitoring may include the use of artificial intelligence (AI) to invoke pattern recognition in order to identify anomalies in the use of the devices or their locations, the patient's physiological and psychological reactions and also to ensure compliance. Neural networks can, for instance, be taught using small data sets based on types of drugs, dosages and geographic location.

Thus, dosage levels may be remotely adjusted automatically based on gathered data or may be adjusted by authorized persons such as physicians acting on behalf of a patient in response to gathered data or in response to a user requesting an adjustment or in response to optional sensor data which measures the user's biological or psychological reaction to the substance.

According to one aspect of the invention, the communication of data from devices (e.g., regarding user compliance, device location, biological or psychological reaction, and the transmission of information to devices, (e.g., to adjust dosage levels, or turn off a device in case of suspected abuse, or to authorize each dose in a dosage-on-demand system), is implemented on a blockchain platform and accompanying peer-to-peer network. This ensures secure transmission of patient data, capturing of user compliance data, tracking of device location, authentication of users, and management of dosage regimens for some or all users on a dose-by-dose basis. The blockchain implements the gold standard for user authentication by providing a consensus-based system. The use of a blockchain to implement the present invention allows:

authentication by consensus of a patient request for a dose;

sharing of dose transaction history among devices, agencies, physicians and judiciary boards;

sharing of optionally anonymized dose, frequency and user genetic, physiological and psychological reaction data for research and analysis purposes to improve and hone substance composition and substance combinations to further the development of such substances and combinations and to further substance innovation in general.

transmission of patient records in a secure manner while maintaining patient anonymity, and aggregation of information from all participants (patients) into reports that can be disseminated to appropriate authorities/recipients as needed.

By capturing use location, physiological and psychological reaction data from all devices it allows for big data analysis to identify anomalies and potential abuse or need for intervention in the use of a device by a patient, e.g., by remotely switching off the device.

Through the use of geo-location sensing, this system makes it possible to obtain an overview of where drugs are located at any time, from the time of dispensing by a physician, hospital or pharmacy, to the use and return of the device by the user. The geo-location sensing may be included with a blockchain implementation, allowing for a blockchain-based hack-resistant chain-of-custody for logistics, inventory control, audit and security considerations to ensure data and instruction integrity.

Thus, the present invention provides for real-time or near-real-time big data aggregate reporting capabilities, and of user behavior analysis and biological or psychological reaction analysis and pattern recognition by reading from a blockchain-based distributed database. This provides control over the dispensing of prescription drugs and facilitates remote dispensing. The delivery device may either be programmed to dispense according to a defined schedule (defined times and dosages), which can be adjusted based on feedback data, or the dispensing of a drug by a device can be authorized on a dose-by-dose basis.

As indicated above, this controlling of valuable and high-risk substance is not limited to opioids or other drugs but includes monitoring, tracking, and remote dispensing of any expensive substance or material.

Geolocation keeps track of the location of dispensing devices at all times, while automated reporting and alerting for each use or uncharacteristic use ensures monitoring of the contents of the devices and the locations of dispensed or released substance/material.

This becomes particularly important with expensive specialized substances whose use needs to be monitored or where inventory needs to be tightly controlled, even where it is used only internally within a company or distributed for research purposes such as venom (which can cost as much as $300,000/oz), or powdered plutonium ($4,000/gram), or samples of virus/infectious agents whose use needs to be monitored.

The present invention thus includes two further features: inventory management, and on-demand billing. This allows, for example, for users to be billed only for what they use and ensures that unused portions of a product can be returned, e.g., by a predetermined date.

Also, by aggregating the data from all devices for a particular substance or class of substances, it allows for user behavior and reaction analysis, analysis of the geographic distribution of such behavior, and oversight over inventory use and withdrawal.

Further, according to the invention, there is provided a pulmonary delivery device for pulmonary self-administration of prescription drugs such as opioids, e.g., methadone, to facilitate OUD MAT (opioid use disorder medication assisted therapy) for use in recovery.

The device may include a biometric sensor for local user authentication before it will dispense a dose, and to limit dispensing to a time schedule determined by the physician's prescription, which may be stored on the device.

The device may also include or communicate with off-board biological sensors which take measurements of the user physiological data, such as body core and peripheral temperatures, EEG, ECG, EMG, blood pressure, pupil size, or skin conductance, recording the user's biological state before, during and after a dose.

The device may also include or communicate with environmental sensors to detect and record pertinent environmental measurements such as ambient temperature, humidity, G-forces, etc.

The device may also include means for logging each dose when it is dispensed and the patient's physiological and psychological responses and the environmental data and transmitting the logs to the physician. The means for logging may include one or more sensors to monitor the amount of drug used, one or more sensors to monitor physiological and psychological reactions and environmental measurements, a controller, and at least one of data memory and a communications means (e.g., cell phone, Bluetooth, Internet, etc.). Compliance and statistical reports can be generated for the treatment of patients, for government oversight, insurance, and law enforcement agencies. The logs may be delivered at time of dispensing via the communications means communicating via a network, e.g. client-server network, or peer-to-peer network, which may include a blockchain platform. The logs may also be stored in the data memory on the device for subsequent downloading or for delivery at a later point in time, e.g., when WiFi or cell phone access is available, depending on the type of communications system included with the device.

Still further, according to the invention, there is provided a drug dispensing device that includes a reservoir for a drug, an atomizer for delivering the drug in particle format suitable for pulmonary delivery to the lungs of a user, and communications means for transmitting data to one or more locations, regarding at least one of: time of dosage delivery, amount of dosage delivered, and location of the device, and for receiving drug adjustment or other device control information. The communications means may be arranged to communicate using a peer-to-peer network and blockchain platform.

The device may include geolocation circuitry to allow the device to be located, e.g., RFID readers, GPS circuitry, or any other circuitry that allows the location of the device to be sensed by external sensors or signals, or communicated by the device continuously, or at predefined times in order to save power.

The device may also include one or more local user-authentication means, such as a biometric sensor, e.g., fingerprint or retinal scanner.

The communications means will typically include a receiver for receiving information, such as dosage levels and delivery times, or adjustments to dosage levels or delivery times, or to control the operation of the device, and it will typically include a transmitter, for transmitting data regarding one or more of the identity of the user or data for validating the identity of the user, location of the device, times, and amount of drug dispensed. The communications means may include a local communications means, such as Bluetooth to communicate with a secondary device such as a smart phone, which in turn may form part of a peer-to-peer network, or the communications means may include cell phone or internet communications circuitry as part the device to deliver data and receive information directly.

The reservoir for the drug or the entire device may be provided with a tamper-resistant housing. The reservoir may, for example, include a housing that encases the reservoir and releases a chemical to render the drug unusable in the event of tampering with the housing.

DETAILED DESCRIPTION OF THE INVENTION

Figure 1:
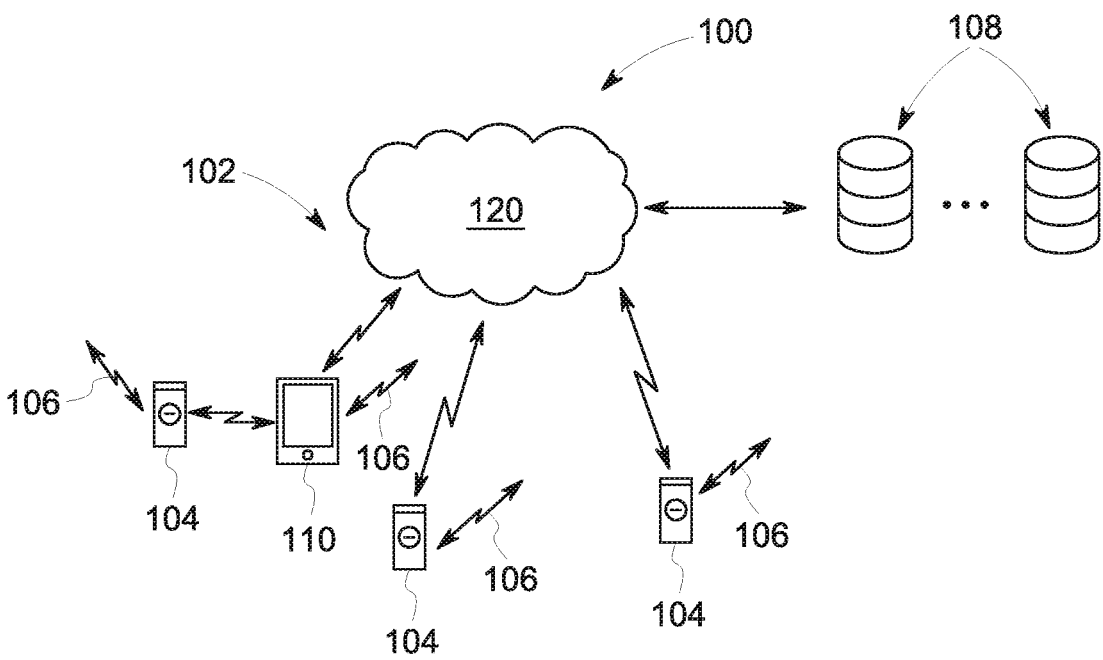
FIG. 1 shows a schematic representation of one embodiment of a system of the present invention.

One embodiment of a system of the present application is shown in FIG. 1. In order to implement a system 100 of the present application, the system requires a secure communications network 102, which is preferably built on a blockchain platform; one or more tamper-resistant delivery devices 104 for the conveyance and dispensing of a drug or other valuable substance/product; locating means 106 for tracking the devices 104 (e.g. using GPS, or secondary locating devices such as RFID readers or chips) and management means 108 in the form of one or more servers and databases acting as an administrative platform for data creation, maintenance, and monitoring and generally controlling the network, devices and dispensing of the product, and as a data warehouse for capturing data and performing one or more of tracking delivery devices 104, monitoring users and the dispensing of substance, aggregating of data, reporting, pattern recognition, data mining, archiving and dissemination of reports and data.

Several embodiments involving the delivery of a prescription opioid will be discussed below, but the invention includes inventory monitoring, authentication and tracking of other substances and materials as well.

In one embodiment of the system, a delivery device 104 communicates with a secondary, network-connected, communications device 110 such as a smart phone or personal computer (PC), using a local communications system such as Bluetooth, or via WiFi, etc. Insofar as one or both devices 104 and 110 contain embedded GUIDs (globally unique identifiers), potentially embedded into RFID tags within the devices 104, 110, these may also be used to assist in locating and tracking and inventorying the devices 104 both locally using RFID readers and remotely using the embedded GUIDs transmitted over the network 102 in response to a network query such as a request "identify yourself".

As part of initial authentication of the user, one embodiment includes a downloadable app (application) that a user downloads onto a smart phone or PC and which then communicates with a device by any communications means supported by the smart phone or PC and the device, e.g., Bluetooth, RFID chip and reader, cell phone, etc. Initial authentication and enrollment of the user can take place using conventional identification means, e.g., photo ID such as a driver's license, allowing the device-issuing authority e.g., the pharmacist or physician to associate a device 104 and drug-containing housing or a replaceable cartridge that fits onto or into the device 104, with the authorized user. Or an initial authentication may provide permission for a user to download an app, followed by direct communication between the app and the device to define operating conditions, e.g., authorized doses, schedules for dispensing of the drug, and authorized locations for use of the device. This authentication process of new users thus serves as one method of securely enrolling new users into a program that gives them access to a network-connected device.

A device 104 may also include a genetic-sequencing component, which during daily use or during user enrollment may measure the user's sensitivity to the substance dispensed via device 104 and use this genetic-sensitivity data to scale dosages, either automatically or manually by a pharmacist, physician or practitioner in order to prevent overdoses or ineffective dosing due to individual user sensitivity to the contained substance. In one embodiment, upon initial registration and use of the device and potentially periodically throughout the course of the use of the device, the user will perform a genetics-calibration process whereby they will provide a genetic substance sample e.g., by placing their tongue on a saliva sensor on the device, e.g., embedded in a cap covering the substance delivery port/mouthpiece of the device. The sensor, in this embodiment, accepts and analyzes the sample using an integral or external on-demand genetic-sequencing component such as the prior art sensor: SmidgION by NanoPore, which is discussed in more detail at (https://nanoportech.com/products/smidgion.) The genetic-sequencing component in turn reads the sample and generates output containing the genetic sequence of the user, feeding that sequence into the system as a stream of data. The system (which includes controllers: in the form of local controllers on the devices 104, distributed controllers, e.g., by virtue of the interaction of the devices, and/or centralized controllers, e.g., as part of the management means 108) analyzes the genetic sequence by scanning the data for specific genetic markers and patterns which indicate and provide metrics estimating the user's genetic sensitivity to the substance to be dispensed by the device (and possibly other sensitivities and pre-dispositions). The system converts these metrics into one or more substance scaling factors and stores pertinent genetic markers and patterns and derived scaling factors with the date and time of the measurement and analysis in the user records locally and/or on the blockchain. The metrics may also be used to generate reports for use by authorized parties such as the patient's physician. Subsequently, when the user requests an inventory withdrawal (e.g., requests a dose of substance) the controller retrieves the sensitivity scaling factor and genetic marker and pattern history from the user data stored locally in the device and/or on the blockchain. The controller may calculate a new scaling factor from the genetic information, and/or use the stored scaling factors and apply one or more of these to the user dosage schedule to adjust the dosage before dispensing, thus automatically scaling each dosage based on the user's sensitivity to the substance. This process provides the device with the ability to predict with a degree of accuracy an individual user's response to a given dosage, and before dispensing adjust the dosage based on the user's sensitivity to the substance in order to optimize the use of the substance, and/or the user's experience and also prevent under-dosing, overdosing, injury, inefficacy or dissatisfaction. The devices 104 thus allow users' sensitivity, not only to a particular drug, but generally based on their genetic profile and their risk and associated health to be monitored remotely and on an on-going basis. It will be appreciated that the genetic information may also be used to validate the user's identity from time to time.

Similarly, bio-feedback components, e.g., heart-beat monitoring sensors, blood-oxygen monitors, core and peripheral body temperature sensors, brainwave/nervous system monitors, pupil dilation monitors etc., may be included with the device 104 or be provided as an adjunct configured to communicate with the device 104, e.g., by Bluetooth, so that the data from the sensors/monitors can be used to monitor a patient's health generally and, more specifically as regards the drug being delivered by the device 104, to automatically (or manually in conjunction with a pharmacist, physician or practitioner) adjust the device dosage delivery schedules and scaling factors to improve dosage safety and efficacy.

By connecting to a network (typically the Internet 120) in real time, patient usage and dosages can be monitored and adjusted in real time to address patient-specific issues. This also allows all dosages and volumes of dosages to be indelibly recorded via blockchain inventory records and balance ledgers so none of the drug is left unaccounted for. It also allows dosage control schedules to be adjusted by the physician to ensure patients do not overdose, while gradual tapering can be implemented in real time to wean patients off the drug and prevent dependence.

Capturing the information in a central or distributed database 108 also allows reports to be generated and auditing to be performed without difficulty, cost-overhead, or delays. This allows all critical participants to be provided with relevant information: from physicians, nurses and hospitals needing to care for patients, to pharmacists and dispensaries that need to track inventory and drugs going out, to insurance providers needing to validate and manage costs, to regulatory authorities, legal support, law enforcement, and government entities in order to allow oversight and intervention in the case of drug abuse and other problems.

It will be appreciated that in a preferred embodiment, based on a blockchain platform, the data and user information will, by definition, be stored in a distributed database 108 which makes the system hack-resistant and also provides a distributed form of user authentication, as is discussed in greater detail with respect to the next embodiment.

Figure 2:
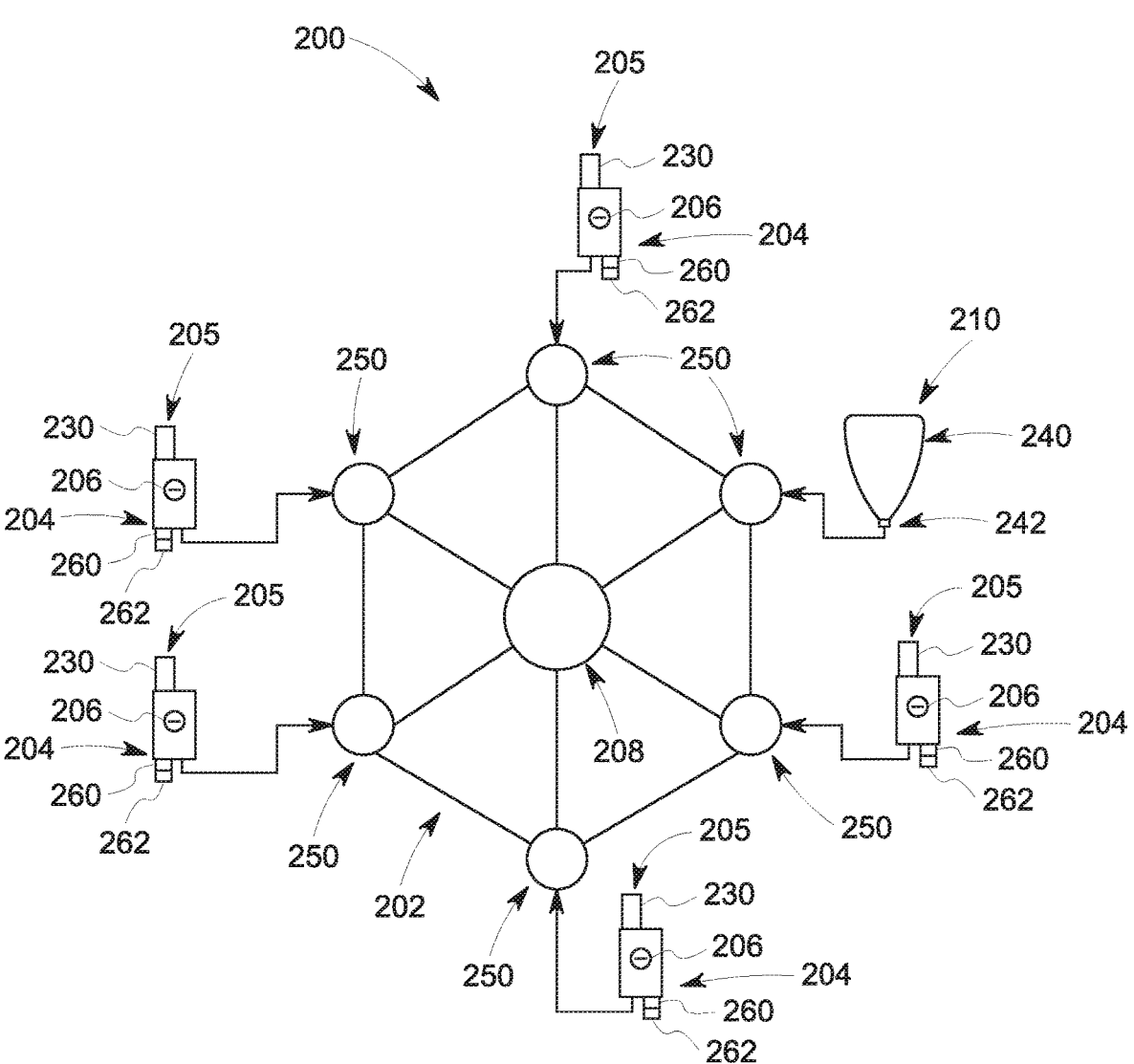
FIG. 2 shows another embodiment of a system of the invention.

Another embodiment of a system 200 of the present application is depicted in FIG. 2 and includes clients 204, 210 connected via one or more networks 202, which may include the Internet, to one or more servers 208. As discussed above, the term "client" is used herein to include both user delivery devices 204 as well as filling stations 210 (also referred to herein as replenishment devices). The filling stations serve to replenish drug reservoirs 230 in devices (e.g., by pharmacists, device-manufacturers, or device-recycling entities).

The dispensing devices 204, filling stations 210, and servers 208 define inter-communicating nodes 250 in the network 202.

In order to avoid abuse, the devices 204 are protected by user-verification components. When a user attempts to use a device 204, the verification components attempt to identify the user and determine if the user is recognized and authorized to perform the particular function with the device, inter alia by consulting local and/or distributed data sources (also referred to herein as remote data sources), including consulting other devices on the network. If a user is determined to be authorized to dispense the substance, the device determines the maximum amount that the user may receive and dispenses an authorized amount and quantity of the contained substance optionally up to the maximum amount determined to be authorized at that time for that user.

The identification and access determination logic in this embodiment are implemented both locally (e.g. a biometric sensor such as fingerprint scanner 206 on the device) and remotely using a network of participating nodes 204, 210, 208 and blockchain technology to prevent hacking, which is discussed in greater detail below.

In this embodiment, the substance being dispensed is housed in a replaceable cartridge or reservoir 230. At least one of: the device 204, and the reservoir 230, is reinforced to resist tampering, and if tampered with, the substance in the reservoir is denatured (as discussed in more detail below) to render it ineffective, unusable, or undesirable.

The re-filling or replenishment of reservoirs 230 (which may be replaceable reservoirs that can be removed from the rest of the delivery device or may be formed as part of the delivery device) may take place in a manufacturing or recycling facility or may be distributed, e.g., delegated to pharmacists.

In the latter scenario, a replenishment device 210, can take the form of a container with a delivery port 242 that is configured to complementarily engage an access port on the reservoir 230 to fill the reservoir 230 of the dispensing device 204.

It will be appreciated that, depending on the substance being dispensed, secure and hack-resistant combinations of replenishment devices 210, delivery devices 204, and process permits will be necessary in order to control the dispensing of such substances.

In one embodiment, the system includes the following components and sub-components:

1. At least one dispensing device 204, composed of:
   a. Dispensing mechanism having a mouthpiece or dispensing port 205 (which is discussed further below),
   b. Local user identification component, e.g., Biometric sensor 206 with interlocks to disallow access to unauthorized users,
   c. Substance reservoir 230 to house the substance (which may be replaceable),
   d. Local controller to control the operation of the device based on information received via the network 202 and from local sensors such as the biometric sensor 206,
   e. Local storage component with local data store, connected to the controller to capture data from the sensors (such as dose volume sensors) and for storing control programs such as delivery schedules and dosages,
   f. an embedded or external communication component which can read/write data from/to network 202. (For purposes of this application the term embedded communication component refers to a communication component that is included in the device 204 to allow the client to communicate with remote clients directly, e.g. via WiFi or cell-phone. Instead, as discussed above, the communication component may include a local communication means, e.g., Bluetooth, configured to communicate in conjunction with a secondary communications device such as a cell phone or PC, to allow communications with remote clients via the secondary communications device. For ease of reference this second type of communication component will be referred to herein as an external communication component.

g. Physiological and psychological sensors 260.

h. Environmental sensors 262.

2. Peer-to-peer network(s) 202 (which preferably uses a Blockchain data storage format) providing inter-node connectivity for communications between nodes 250 (which are defined by the devices 204 and filling stations 210) and one or more administrative nodes, data-consumer nodes, audit nodes, and data-warehousing nodes, collectively depicted in FIG. 2 by reference numeral 208 and discussed in greater detail below.

3. One or more data warehousing nodes 208 (which aggregate data for analysis and later reference and reporting, analysis and pattern recognition), each composed of:

a. Warehouse programs for loading, aggregating, analyzing and performing pattern-recognition of data received from clients, to allow reporting on such data.

b. Warehouse datastores containing the data c. An embedded or external local communication component which can read/write data from/to network 202.

4. One or more administrative nodes (performing ERP—enterprise resource planning—which functions to create, manipulate and report on data records gathered from the clients and to disseminate such information), each composed of:

a. Administrative programs and reports b. Operational usage programs and reports c. Administrative and operational datastores (The administrative nodes may perform analytics, e.g. using AI systems to detect anomalies in the operation of the clients, and may be included with the data warehousing nodes or implemented separately)

d. An embedded or external communication component which can read/write data from/to network 202.

5. One or more audit nodes (which may be implemented using one or more system-provided APIs (application program interfaces) and may include hardware—in order to audit system data, transactional data, master data and configuration data to ensure integrity of the operation of the system, the clients and the network, as well as compliant handling and monitoring of user data and integrity of network activity, and auditing of blockchain activity, user and client activity, device usage and substance tracking), each composed of:

a. Auditing code b. Auditing datastores c. And an embedded or external communication component which can read/write data from/to network 202

6. One or more data consumer nodes (an optional service to provide specialized reports for use by law enforcement, government agencies and insurance companies—which may again be implemented using one or more system-provided APIs), each composed of:

a. Data-consumption programs b. Data-consumption datastores c. And an embedded or external communication component which can read/write data from/to network 202

7. At least one filling station or replenishment device 210, composed of:

a. A substance-housing or container 240, b. Docking mechanism with dispensing port 242 to dispense substance from the container into device reservoirs 230, c. Dispensing mechanism, which may simply be a flow conduit with an electronic valve controlled by a controller, d. Local user identification component, e.g., biometric sensor for pharmacist authorization, with interlocks to disallow access to unauthorized users, e. Local controller, f. Local storage component with local data store for the replenishment device.

g. an embedded or external communication component which can read/write data from/to network 202

Generally speaking, these components are structured such that there are six main component types connected to each other via a network. These include dispensing devices, filling stations/replenishment devices, data-warehousing nodes, administrative nodes, audit nodes, and data-consumer nodes.

Within a dispensing device (or delivery device) 204, substance reservoirs 230 are connected to dispensing mechanisms (e.g., piezo ejector assemblies) via interlocks. Interlocks and dispensing mechanisms are connected to local controllers which control the dispensing mechanisms to release the substance and signal the interlocks to either lock or release the substance from the containers or control the operation of the dispensing mechanism (e.g. in the case of a piezoelectric ejector mechanism, the controller may control a piezoelectric actuator).

For each client, the local user-identification components are connected to the local controllers, as are the local storage components which contain the local datastores. The local controllers are also connected to the networks via an embedded or external communication component. The network is thus comprised of a co-operating set of user identification and control components which are each connected to distributed (remote) storage components containing remote datastores.

In this embodiment there is also a filling station or replenishment device 210, which can simply be a substance container 240 with outlet port 242 and user authentication and interlock to allow only authorized personnel to dispense substance from the replenishment device. In another embodiment, the replenishment device 210 can have a structure similar to that of a dispensing device 204, with additional interlocks and docking mechanisms, where the docking mechanisms are connected to the dispensing mechanisms via the additional interlocks.

The dispensing devices 204 and replenishment devices 240 are connected via one or more networks 202 to distributed controllers in nodes 250. In the distributed (remote) nodes the distributed (remote) storage components which contain the distributed (remote) datastores are connected to distributed (remote) controllers (which are included as part of the devices 104 and filling stations 210 that define the nodes 250), as are the remote user identification components.

This architecture allows the system to identify and determine in real time if a user e.g., patient using the delivery device; or the pharmacist using the replenishment device) is authorized to dispense the substance and if so to authorize the client to dispense while exerting degrees of control over the amounts and quantities dispensed.

As mentioned above, the term user is not limited in every application to a human user. In certain circumstances it may include a non-human, or hybrid user. The term non-human user includes any type of non-human user, such as a physical or virtual device or machine/robot (bot), which may include either a hardware or software bot. In one embodiment the bot could be either the recipient or an intermediary (proxy for the final recipient.) For example, a bot may receive and handle medication to re-dispense to humans (e.g., a bot at Amazon, or bot-pharmacist) or it may function in place of a human user, e.g., to handle virulent bacteria or radioactive substances on behalf of human end-users. In the case of an artificial intelligence (AI) controlled bot, it may be performing autonomous research. By making use of a system of the present application, the bot may order one or more drugs or substances using one or more devices and then dispense and combine such substances in new and unique combinations to create new discoveries.

In order to accomplish the desired objectives, the system includes software to determine if the user is recognized, and further if the user is authorized to dispense the substance or replenish via the replenishment device at a particular time, and if so, determine the amount for which the user is permitted to dispense or replenish at that time, and then control the delivery device or replenishment device to permit the user to dispense or replenish that amount.

This software runs on the local or remote controllers, or a combination of local and remote controllers, accepting input from the identification components on the devices and using the local or remote controllers and datastores to determine if the user is authorized to dispense the substance, and to determine the permitted amounts.

In a preferred embodiment the dispenser includes software that identifies the user which then determines if the user is authorized for that substance at that time and in what amount, and only then dispenses the authorized dosage to the authorized user at the authorized time.

Figure 3:
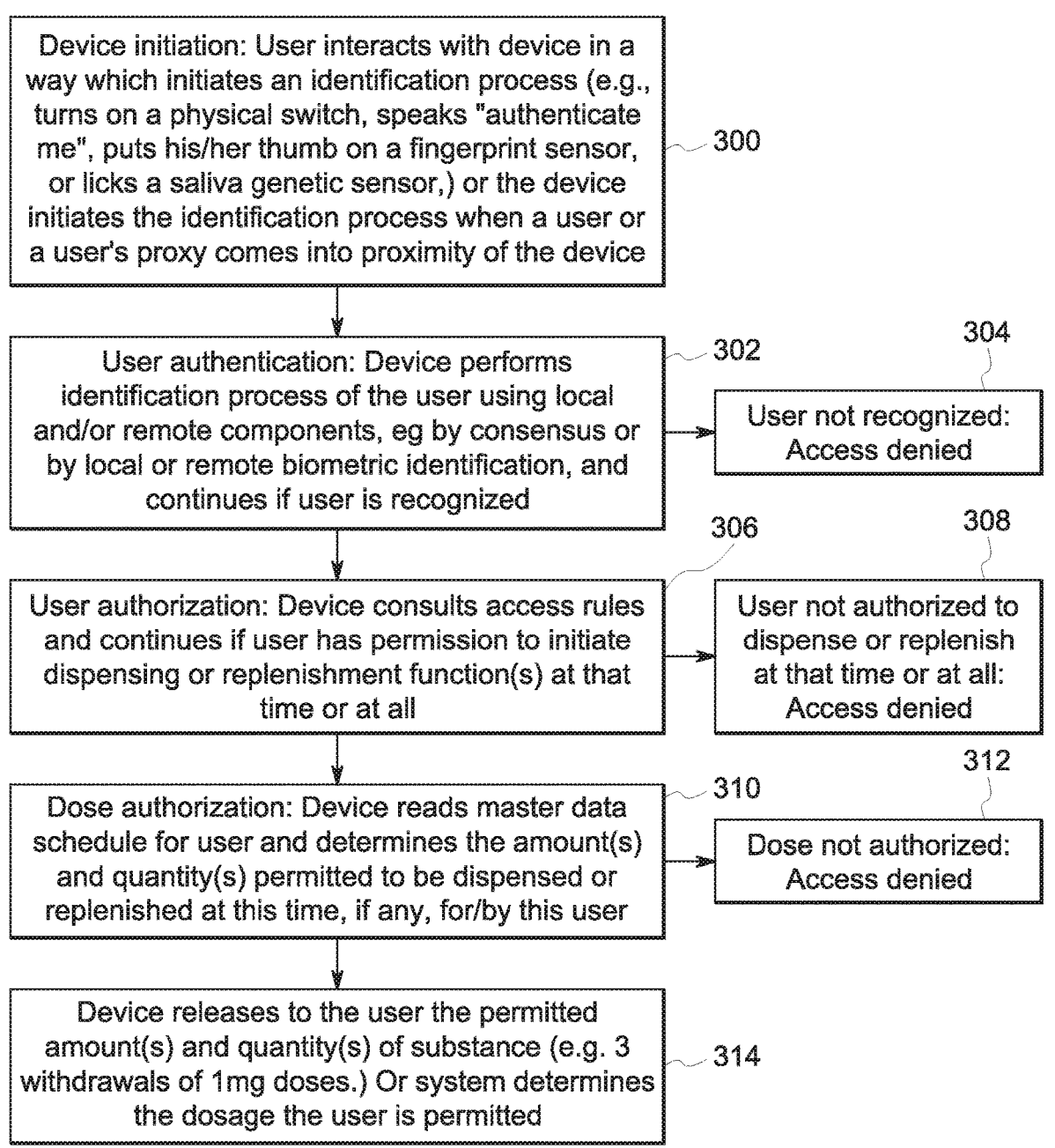
FIG. 3 is a flow chart defining the logic of one embodiment of user authentication and dispensing authorization.

In one embodiment, shown in the flow chart of FIG. 3, the logic performed by the local and/or remote controllers includes the steps of:

Device initiation 300, which may take place in different ways. In one embodiment, the user interacts with the device in a way which initiates an identification process (e.g., turns on a physical switch, or speaks into a microphone, saying "authenticate me", or puts his/her thumb on a fingerprint sensor, or licks a saliva genetic sensor). In another embodiment the device initiates the identification process when a user or a user's proxy comes into proximity of the device.

User authentication 302 in which the device performs an identification process of the user using local and/or remote components, e.g., by consensus or by local or remote biometric identification, and continues if user is recognized. If the system fails to authenticate the user (block 304) access is denied.

User authorization, 306 in which the device consults access rules and continues if the user has permission to initiate dispensing or the replenishment function(s) at that time. If the user is not authorized to dispense (block 308) the material at all or is not authorized to do so at that time, access to the material is denied. Thus, the device will not dispense material to the user.

Dose authorization 310, in which the device reads master data schedule for the user and determines the amount(s) and quantity(s) permitted to be dispensed or replenished at that time, for the user. If the dose is not authorized (block 312), the user is denied access to the material.

Material release 314, in which the device releases to the user the permitted amount(s) and quantity(s) of substance (e.g. 3 withdrawals of 1 mg doses), or if the system defines the dosage on a dose-by-dose basis, the system determines whether, and what amount the user is permitted to receive.

By authorizing users prior to use of a replenishing device or delivery device the system maintains a verifiable chain of custody for the substance.

For greater flexibility and to permit input from various authorities with a vested interest in the tracking and control of the substance, several overrides may be included in the logic. The associated computer process in one such implementation of the method of the present application includes the following executable steps as shown in the flow chart of FIG. 4.

1. Authentication of the user by biometric or a combination of biometrics 400,
2. If identity of the user is confirmed 402, the applicable master data substance-release schedules is read 404 from the blockchain,
3. The amount of substance that may be released (dispensed) at that time is verified based on one or more of:
   a. a substance release schedule which determines whether the release of substance is permitted at that time (block 406), and which may consult previously logged transactions and uses them to contribute to the outcome of the decision,
   b. a substance amount and quantity schedule which determines the permissible amounts and quantities of substance to be released, issued or dispensed at this time (determines whether the dose has already been taken) (block 408).
   c. If dose has not yet been taken (branch 410), is there an override 412 of the schedule by an on-demand authorized agent (which represent agencies tasked with oversight of the substance) that must be consulted to permit the release at this time,
   d. If dose has already been dispensed at that time (branch 414), no further dose will be permitted unless an ad hoc override of substance 416 is authorized without the other condition needing to be satisfied (e.g. an override by a user's physician inserted into the workflow to grant a dose that was not previously specified in the pre-programmed scheduling software)

In addition to biometric authentication, the system may include remote authentication of the user by consensus via the peer-to-peer network. This is discussed further below with respect to FIG. 5.

In the preferred embodiment, the software which encodes and disseminates permissions and delivery schedules operates via a blockchain so that the data will be hack-resistant and adds a layer of remote authentication by checking the user's permissions by requesting consensus from the blockchain network participants, thereby making the authentication process hack-resistant as well.

This involves one or more challenge-and-response messages sent to the client device from a set of peers on the network which may be randomly selected or selected by specific criteria. The challenge may be answered by the device directly or may be required to be passed to the user of the device who must then input a response to the device which in return relays the response back to each requestor. The requestors as a group may further communicate with each other or other peers to decide if the aggregation of responses satisfy the requirements sufficiently to provide positive identification of the user and/or device, and if they reach consensus, all peers send back their own go-ahead signal permitting the release of substance. The peers may also choose to act independently and decide their own response independently from the rest. The peer-to-peer client device receives back the responses and using a consensus algorithm will make the final go-no-go decision.

Figure 5:
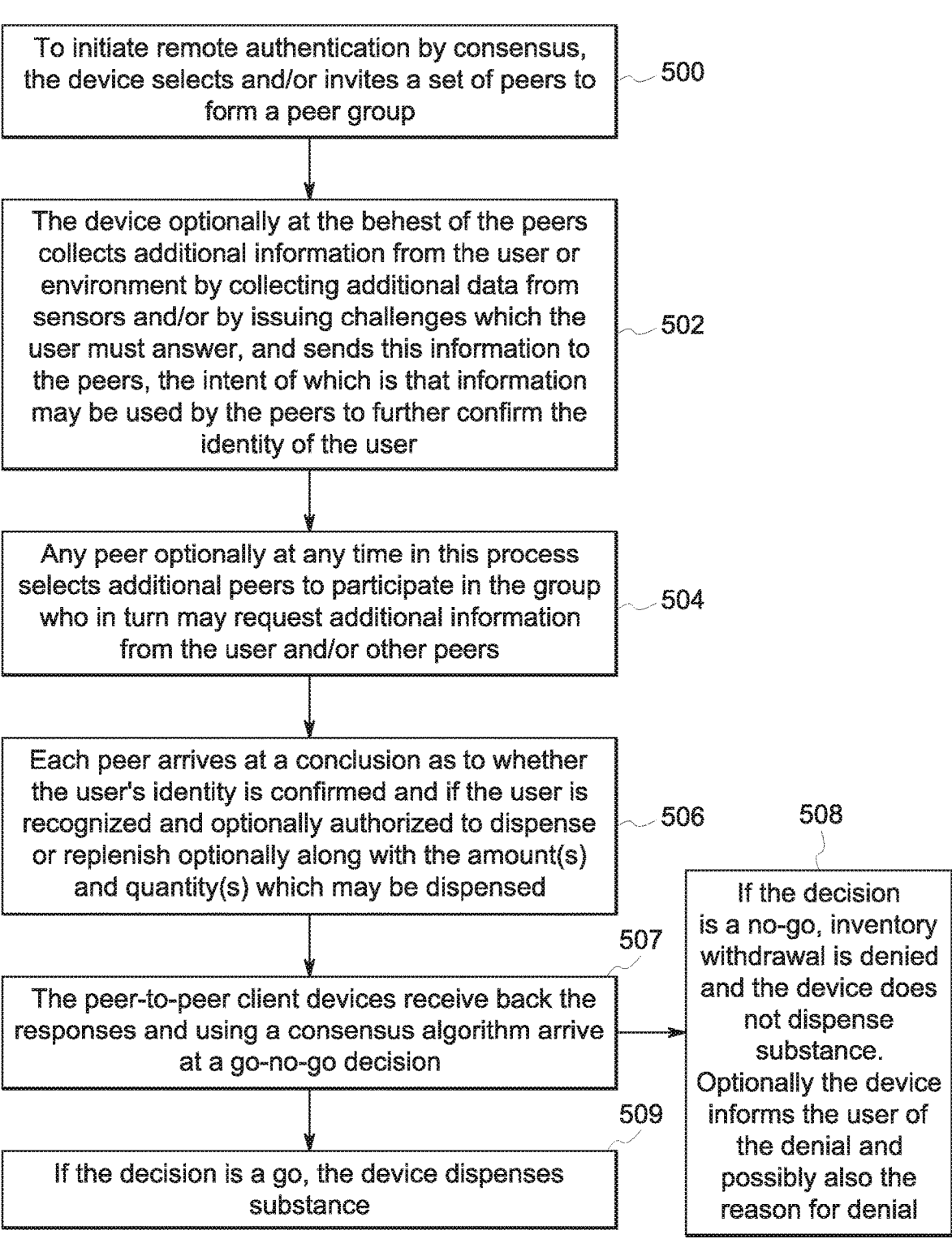
FIG. 5 is a logic diagram of one embodiment of the logic involved in peer-to-peer authentication and verification.

The logic involved in one such embodiment is shown in FIG. 5 and includes the steps of:

Initiation 500 of remote authentication by consensus, in which a device 104, 204 or filling station 210 selects and/or invites a set of peers to form a peer group.

Optionally, at the behest of the peers, the device then collects additional information 502 from the user or environment by collecting additional data from sensors and/or by issuing challenges which the user must answer, and sends this information to the peers, the intent of which is that information may be used by the peers to further confirm the identity of the user.

Any peer may optionally, and at any time in this process, select additional peers 504 to participate in the group who in turn may request additional information from the user and/or other peers.

Each peer arrives at a conclusion 506 as to whether the user's identity is confirmed and whether the user is recognized and whether that user is authorized to dispense or replenish, and the amount(s) and quantity(s) which may be dispensed.

In step 507 the peer-to-peer client device receives back these responses and using a consensus algorithm makes the final go-no-go decision.

In step 508 the device uses the consensus decision. If the decision is a go, the device dispenses substance. If the decision is no-go it does not dispense substance.

Authorization is thus based on a consensus or on a critical mass of authorization by the peers according to a consensus algorithm as known in the art.

In addition to the hack-resistance of the present application, the devices 104, 204 and filling stations 210, may include physical tamper resistance.

In one embodiment the delivery devices 104, 204 and replenishment devices 210 include law-enforcement grade biometric sensors 206 to ensure identification to law enforcement standards, and include tamper-resistant housings for the substance, which may include a secondary housing surrounding the substance reservoir, wherein the secondary housing contains an antagonist or other chemical that is released if the device is tampered with, thereby denaturing the contained substance such that the substance will be rendered unusable for the intended purpose or undesirable for any use.

In one embodiment the security of the design is enhanced through the use of a protective chamber to physically protect the contents. This may include the use of special materials such as cast titanium, coupled with an EMF (electro-magnetic field) shield and an integral lock that is electronically controlled through circuitry from the inside, with the only circuitry extending outside the device being the power leads which supply power to the circuitry, and the wireless antenna. The circuitry may be configured to behave like a Davinci Cryptex, in which the wrong challenge/response codes received via the wireless antenna destroys the contents of the device.

The system of the present application therefore provides a system and method for controlled dispensing of substances such as opioids in a secure and real-time controlled manner, using a tamper-resistant device, with physician-controlled schedules encoded in a hack-resistant blockchain with a hack-resistant authentication consensus process.

The use of a blockchain serves not only to help with user authentication and dosage verification but also provides secure communications and transaction record keeping.

The device 204 or filling station 210 writes one or more transactional records to the blockchain recording one or more of these events. These records are encrypted on the blockchain, potentially using a security certificate for the device and/or for the client or using some other secure method of encrypting records on blockchains.

As discussed above, the benefits of the present application are not limited to the medical field or the monitoring and control of drugs, but includes inventory control, tracking and management of release of any material from a protective housing to an authorized user. In the case of solid materials, the housing may comprise a safe-like structure that includes biometric sensors and communications means similar to the devices 204 discussed above, for purposes of authentication, monitoring and controlling using a peer-to-peer network operating on a blockchain platform.

Benefits of the Present System to the Opioid Crisis:

The present system thus serves to address the opioid crisis in three ways:

1. by preventing overdoses;
2. by preventing dependence; and
3. by curing dependence.

Preventing Overdose:

Each device 104, 204 acts as a tamper-resistant delivery device (in this embodiment, as a drug delivery device), not unlike a syringe but with safeguards that prevent a user from accessing the contents in an uncontrolled manner. In the present embodiment, each delivery device 104, 204 is a pulmonary delivery device in which the particularized drug is delivered to the lungs of a user. The network to which the device is connected, and which captures data and provides control feedback, acts as a virtual nurse and/or administrator, either monitoring or also administering each and every dose in real time via a personalized physician-prescribed opioid schedule. As a safeguard against hacking, or physician, nurse, or pharmacist error, the device may be pre-programmed with a maximum dose for each time interval, e.g. for each day, and will refuse to dispense amounts which exceed predetermined safe dosages and/or the dosage allotment for that drug and patient.

In a preferred embodiment, the device 204 or the drug reservoir/cartridge 230 includes a tamper-resistant casing with anti-hacking protections both physically for the device, and in the network. By using a blockchain-authenticated capture of data coupled with big data analysis to identify anomalies or problems, the potential for abuse and overdose will be greatly diminished and when correctly implemented approaches zero. In addition, this embodiment includes physical tamper protection to deter drug diversion by encapsulating the active substance container (reservoir or cartridge) within a secondary housing that contains an opioid antagonist such as naloxone so that breaching the housing causes the substances to admix thus rendering the active substance undesirable for use and avoiding abuse.

Figure 6:
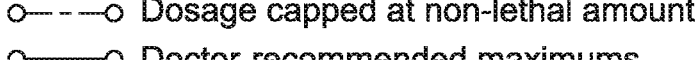
FIG. 6 shows an example graph depicting dosage levels to prevent overdosing, including maximum dosage levels, physician prescribed levels and actual use levels for a patient.
Figure 6:
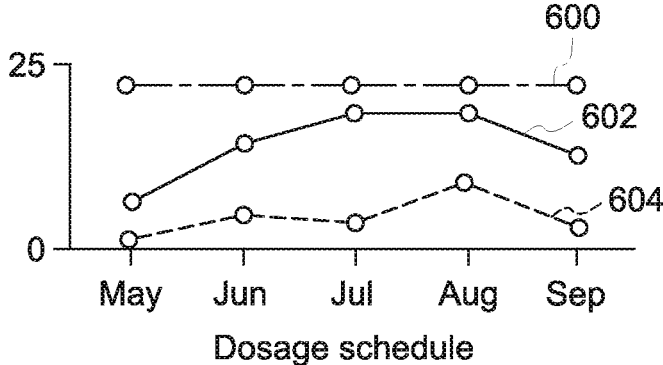

In addition to the maximum levels, which are depicted in FIG. 6 by curve 600, the system in this embodiment allows the patient's physician to intervene and increase or decrease dosages subject to the maximums given by curve 600.

Therefore, since this network functions in real time, a patient who encounters increased pain can request a dosage increase at any time via a handheld device or laptop app. This triggers real time approval workflows, invoking agents, such as physicians, to respond and allowing the device parameters to be modified within minutes, as depicted by the curve 602 in FIG. 6. If the dosage change is denied, the patient is prevented from triggering any additional doses of his or her own volition. Conversely, even if a dosage is allowed, the physician may intervene to reduce the potential maximum doses if for example during remote monitoring the patient displays adverse or unexpected reactions to the substance.

Also, in this embodiment, the device includes miniaturized flow sensors to measure the actual opioid dose delivered by the device. The sensors, which are controlled by a controller, manage not only the dispensing of the drug from the device, e.g., by controlling flow control valves, but also allow the actual amounts dispensed, as defined by the curve 604 in FIG. 6, to be reported back to the network in real time. If a life-threatening flow is reported by the on-device sensor, e.g., due to flow-valve failure, a fail-safe workflow is triggered to issue an alert to agents and first responders, to quickly intervene and mitigate any damage to the patient.
Preventing Dependence:

Patients in pain will typically have good and bad days, but over time, non-chronic care patients need to eventually have their dosages taper off, and usage of opioid discontinued. The physician can set a dose ceiling schedule, which will gradually diminish over a physician-defined time-frame matching the patient's anticipated recovery timeline.

Figure 7:
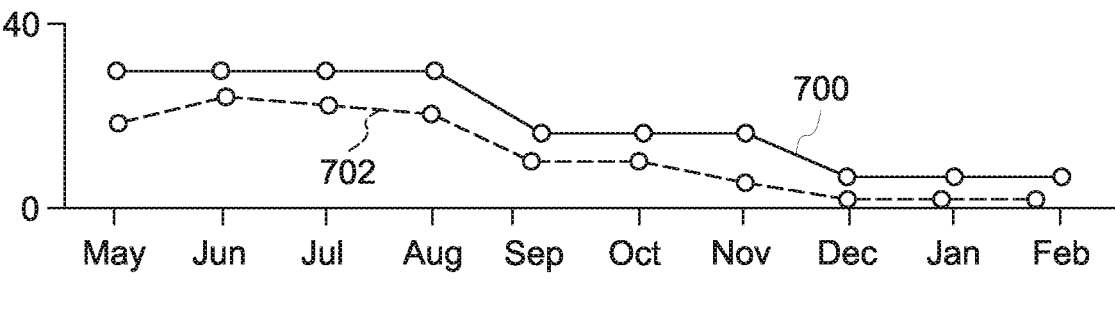
FIG. 7 shows an example of a dosage tapering set of curves to prevent addiction.

The end trajectory of the opioid use can thus be pre-programmed by the physician at the inception of prescription. Barring a deviation from the scheduled trajectory, dependence prevention is virtually guaranteed. In the present embodiment, as shown in FIG. 7, a not-to-exceed maximum 700 is programmed into the device, as well as a physician's tapering-off schedule 702.

As one aspect of the present invention, data is captured in a data warehouse 108, 208 incorporating analytics and reporting tools. In this way relevant reports can be provided to regulatory bodies and agencies of governance, to validate the efficacy of the devices and the program by calculating the number of real lives saved, and the dollar-value of regained productivity.
Curing Dependence:

The third critical benefit of the system of the present invention is the ability to cure opioid dependence. The average person has bills to pay, family commitments, and a life to live, and lacks both the time and the money to take a month off, check into a Betty Ford clinic, and come out cured. The present system provides them with a discrete alternative program which helps them recover their lives.

Figure 8:
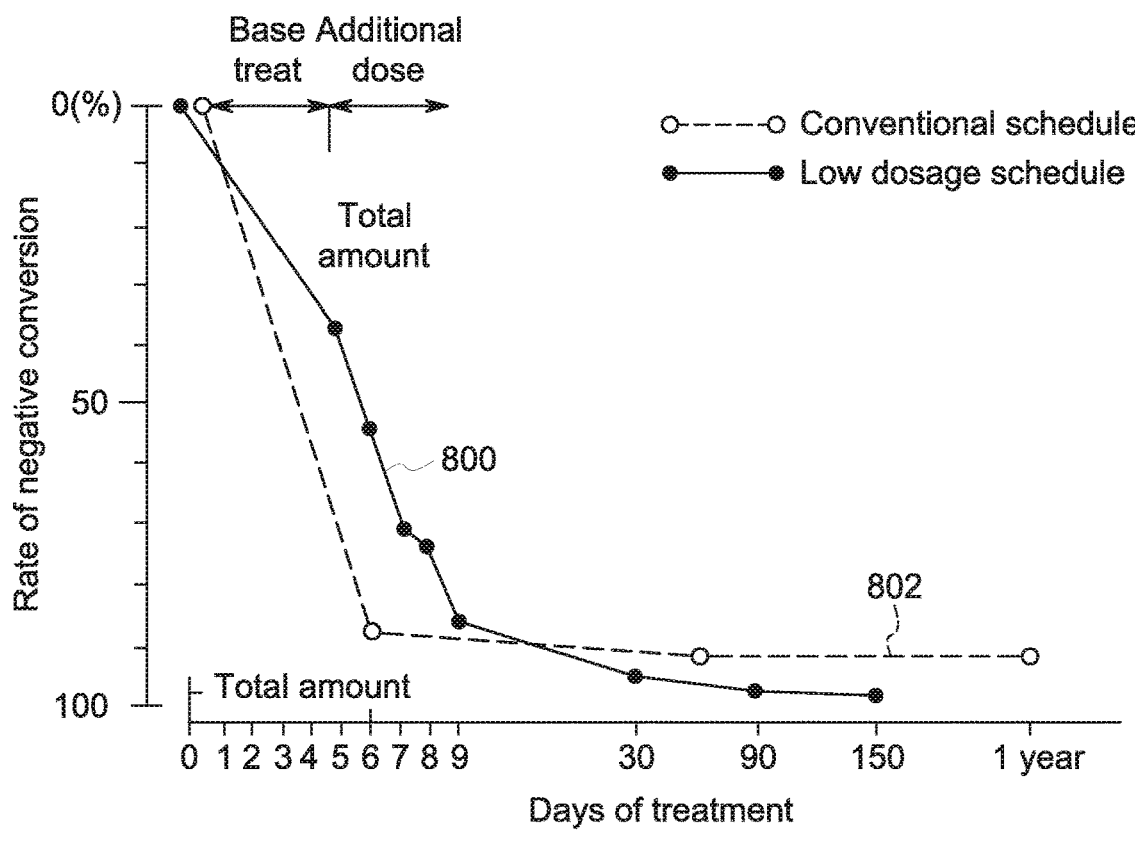
FIG. 8 shows an example set of curves depicting the tapering off of opioid usage in a remotely controlled user recovery program from opioid dependence.

As shown in FIG. 8, a patient can be put on a regular recovery schedule 800, aimed at curing the patient's dependence within for example 90 days, or on a low dosage schedule 802 that will, however, take longer for the patient to reach 100% conversion.

In order to implement the system, one critical element is a tamper-resistant delivery device.

Figure 9:
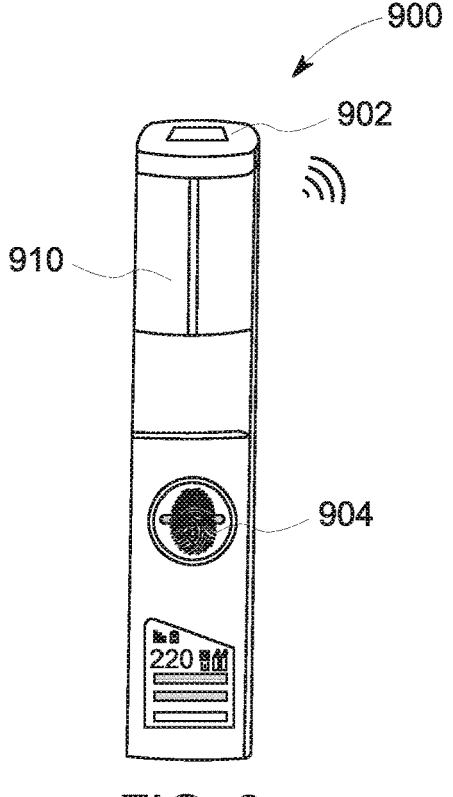
FIG. 9 is a front view of one embodiment of a drug dispensing device of the present invention.

In one embodiment, as shown in FIG. 9, the device 900 is a hand-held, self-contained unit which is portable and makes use of a piezoelectric ejector to aerosolize the drug. One example embodiment of a piezoelectric delivery device is described in U.S. Pat. No. 6,098,620 to Lester, filed Oct. 27, 1995, which is incorporated herein by reference.

In order to ensure consistent dosages, the device 900 may include the ability to measure a variety of patient-specific parameters including the patient's total respiratory tract capacity, inspiratory flow rate and/or inspiratory volume. U.S. Pat. No. 6,098,620 describes a method of drug delivery wherein a patient's inspiratory flow rate and inspiratory volume are simultaneously measured. Information obtained from the measurement is used to release into a patient's inspiratory flow path, particles of the particular drug being dispensed. The drug is preferably released when the inspiratory flow rate is in the range of about 0.10 to About 4.0 liters/second and the inspiratory volume is in the range of about 0.15 to about 3.0 liters. More, preferably the inspiratory flow rate is in the range of from about 0.10 liters/second to about 2.0 liters/second, and the patient's inspiratory volume is in the range of from about 0.15 liters to about 0.8 liters.

In order to ensure delivery of the drug to the lung for optimum systemic effect, the released particles preferably have a particle size in the range of from about 0.5 microns to 12 microns and more preferably in the range of 1 to 5 microns.

For longer-acting sustained-release formulations, the aerosolized particles may be encapsulated in liposomal membranes which slow the delivery to the bloodstream over time and smooth out the user's systemic reaction curves.

The device 900 will typically include a drug-containing reservoir or cartridge 910 and an ejector mechanism for aerosolizing the drug or, in some embodiments, to allow the mixing of pre-manufactured particles with air and/or a gas and/or a delivery fluid. Thus, the ejector mechanism will also be referred to herein as an aerosolizer, nebulizer or atomizer. The ejector mechanism may, in one embodiment, include a piezoelectric ejector (which, in its simplest form includes a piezoelectric actuator and a porous, flexible membrane (e.g., a polycarbonate membrane) as discussed in U.S. Pat. No. 6,098,620.

The reservoir or cartridge 910 containing the drug may, in one embodiment, comprise a multi-dose replaceable cartridge which is in a sealed state prior to insertion into the device and has a breachable wall that is punctured, either at time of insertion or at time of use, as in U.S. Pat. No. 6,098,620, thereby allowing the fluid substance to flow to the porous membrane. A piezoelectric crystal attached to the porous membrane transmits ultrasonic oscillations of the piezoelectric crystal to a resonance cavity and the porous membrane, causing the porous membrane to oscillate and generate a stream of droplets that is caught up in the air flow of the inhaling user.

The device includes an exit port with a mouth piece 902 that creates the air flow through a delivery channel of the device as the user inhales, thereby delivering the particularized drug directly to the lungs.

Since the particle size of the drug, for optimum absorption by the lungs, has to be small, the ejector mechanism of the present application is specifically configured to eject a stream of droplets having an average ejected droplet diameter between 0.45 and 12 microns, preferably 1-5 microns.

In the embodiment of FIG. 9, the device is a handheld device 900 with mouthpiece 902 that is in flow communication with a piezoelectric ejector mechanism. The device 900 includes a fingerprint scanner 904 for authenticating the user.

Another prior art reference dealing with delivery of drugs is published US published application 2018/0110939A1 to Lanzkowski filed Oct. 20, 2017, the entire contents of which are also included herein by reference. US published application 2018/0110939A1 includes a vaporizer to change a liquid to a gas, thus delivering the drug in gaseous form instead of the atomized form delivered by the piezo ejector mechanism of embodiment 900 of FIG. 9.

US published application 2018/0110939A1, however includes biometric sensors to validate users (fingerprint and retina scans) and discusses programming dosage times and tapering off dosages to get people off addiction. Also, it includes a tamper resistant container to render the drug unusable in the event of tampering.

The device embodiment 900 shown in FIG. 9 similarly includes a fingerprint scanner 904 to authenticate the user.

Figure 10:
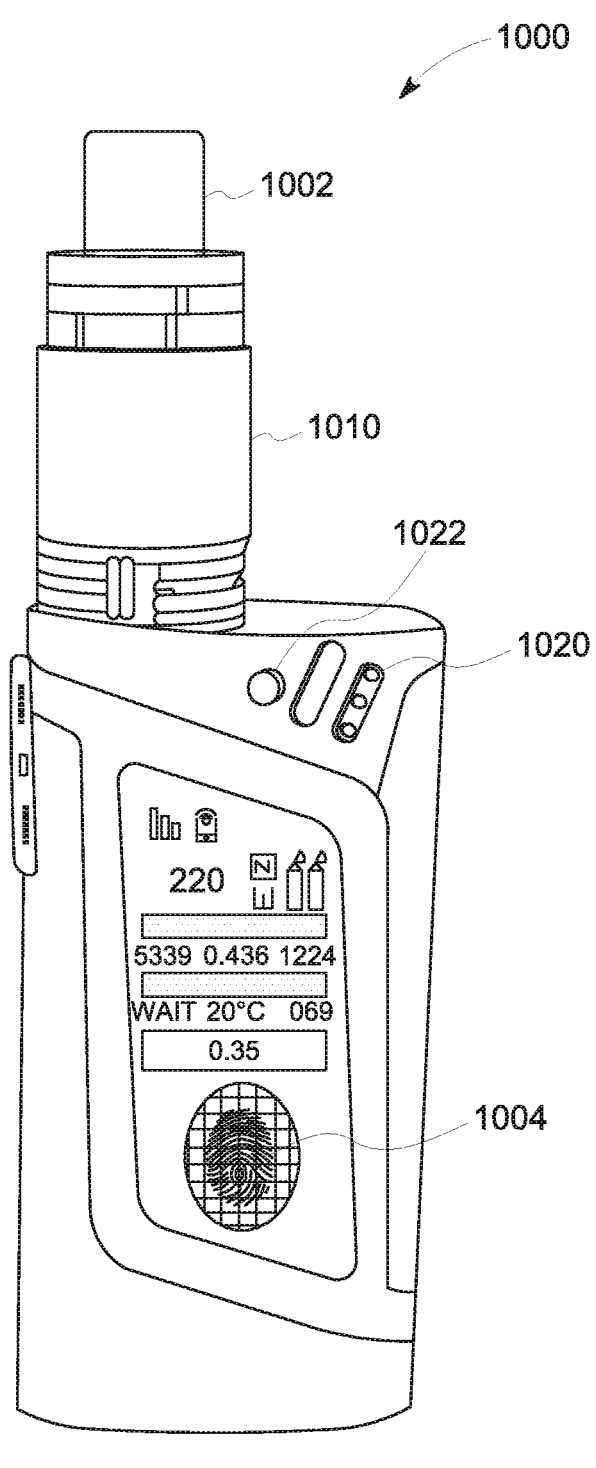
FIG. 10 is a front view of another embodiment of a drug dispensing device of the present invention.

FIG. 10 shows another embodiment 1000 of the device of the present application. Again, it includes a mouthpiece 1002 and a fingerprint scanner 1004. However, in this embodiment the multi-dose replaceable cartridge 1010 is larger than cartridge 910 of the device 900. This embodiment also includes a speaker 1020 and LED 1022 to alert the user of the need to take a dose of the drug. This is a critical feature, especially in pain medication, to avoid the patient waiting too long for a prescribed dose, which results in pain levels swinging to greater extremes and making it more difficult to get pain under control. The speaker and LED can also be used to issue an audible alarm and visual alert if the device detects illicit activity such as tampering or upon exiting its permitted geofence perimeter.

In addition to the features mentioned above, and the elements of the prior art delivery devices discussed above that are included herein by reference, the present invention includes device features and a secure information capture and management system aimed at avoiding abuse of narcotic formulations. This includes a pre-programmed microprocessor designed to avoid overdosing.

Another feature of the present invention designed to deter abuse is the inclusion of geolocation circuitry in the device and to provide geofencing alerts. This may operate as a self-functioning unit, such as a GPS sensor, or operate in conjunction with other devices such as RFID chips or readers on the device, communicating with external RFID readers or circuits.

In a preferred embodiment, the information capture and management system includes an infrastructure based on an encrypted private blockchain. This allows not only secure remote user authentication and dose control, but also ensures secure transmission of data for EMR (electronic medical records).

In one embodiment, the system includes central server software for central patient registration, data collection and dissemination and entry and adjustment of prescription and patient dosage schedules. The various functions may be distributed over one or more of the nodes 250 discussed above.

As discussed above, user authentication may be performed at time of patient registration using conventional photo id. Subsequent authentication of the user during day-to-day use of the device may include user verification using a biometric sensor (e.g. the fingerprint scanner 904, 1004, or a retinal scanner) and/or the application of the blockchain to securely authenticate the user (see further below) and facilitate communications from and to the device.

Figure 11:
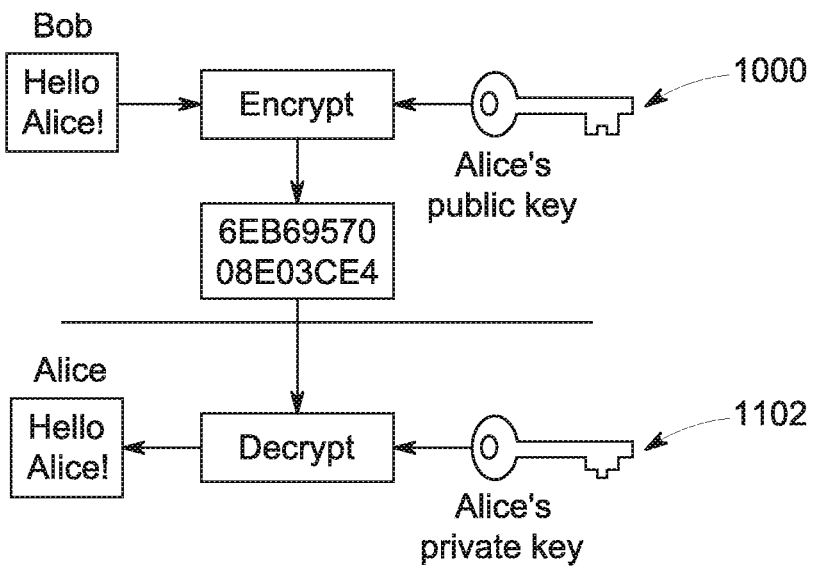
FIG. 11 depicts an asymmetric encryption key system.

In one embodiment user authentication can include the use of an asymmetric key encryption scheme, the concepts of which are illustrated in FIG. 11. The user is provided with a public key 1100 and a private key 1102. During transmission of control information to the device 104, 204, e.g., from the user's physician, to adjust dosage or to permit dispensing of a dose, the information is encrypted using the user's public key 1100 and the user, as the holder of the paired private key 1102, can enter the key into the device, to decrypt the message that instructs the device to operate in the designated manner. Since, in this embodiment, security depends on the secrecy of the private key 1102, and is intended as a user validation device, the private key 1102 could, for instance, be entered into the user's smart phone 110 for direct communication with the device 104 e.g. through Bluetooth. Thus, the location of the smart phone and simultaneous location of the device would serve as confirmation that the authorized user is in possession of the device.

Blockchain:

As mentioned above, one aspect of the present application involves the tracking and managing of devices, which includes capturing and processing information about the devices, their location, operation, usage and users of the devices. In order to efficiently implement such a system, usage of resources is preferably distributed: both for purposes of processing information as well as storing of information. Furthermore, in order to ensure the security and immutability of the information, the system is preferably implemented via a Blockchain.

In order to understand distributed computing and the features that make up a Blockchain it is useful, first of all, to understand cluster computing.

A compute cluster is comprised of a network of interconnected nodes which share the workload. As computing demand increases, administrators add nodes to the cluster and configure load-balancing so that the workload is shared equally among all nodes of the cluster. Cluster computing implements a resource pooling model, wherein physical and virtual resources are dynamically assigned and reassigned according to demand; scalability that provides management with the ability to add more nodes and scale smoothly as demand increases, and resource monitoring, controlling, and reporting, e.g. according to storage, processing, bandwidth, active user accounts, etc.

In the case where many devices connected to the network are physically located far from the cluster and must process many transactions quickly and over a relatively slow and at times unreliable network such as the internet, which may be subject to hacking such as a man-in-the-middle attack, a tamperproof way to transfer data to the central cluster is needed, regardless of the quality of the network connection or ownership of the intervening network hardware nodes.

One embodiment of the present application therefore addresses these problems by implementing a Blockchain system which acts as an immutable and back-resistant specialized database for the data (also referred to herein as information) collected by multiple devices. It validates devices or users of devices, and allows for secure communication with the devices—not only to receive and store information, but also to confer back information to the devices, allowing them to be managed remotely.

The blockchain system can capture data to define blocks in a blockchain for subsequent transmission, analysis, reporting, and control of devices. This may be implemented via a public, private, hybrid, community or other access-level of blockchain, and data may be encrypted for greater security.

One aspect of the present application involves the creation of a Blockchain platform for purposes of tracking, managing and controlling devices and materials, and to verify the identity of users of such devices.

Consider again FIG. 2, implemented as a blockchain system. Thus system 200 in such and implementation defines a blockchain system that includes a central server

208, connected to a collection of dispensing devices 204, each of which includes a processor and memory allowing it to perform calculations and data analysis, add blocks to the chain, and validate new blocks.

In such an embodiment, the blockchain system 200 is implemented as a hybrid system encompassing a central server, which forms part of the infrastructure for the hybrid blockchain, in which multiple dispensing devices 204 and replenishment devices 210 act as nodes in a peer-to-peer network, collecting information and bundling it into new timestamped blocks.

In one implementation, the system 200 includes a network of drug dispensing devices 204 that collect data, and process or analyze the data locally, and may transfer the raw data or pre-processed information to the central server for processing or storing. The data collected in this embodiment includes user identity information (e.g. by virtue of a fingerprint reader on the device or other biometric measurement). The data collected, also includes sensor information to capture medically-relevant information about the user, material dispensing information to track the amount and time of dispensing a dose of drugs by the device, as well as location information.

Another biometric measure may include an oral cavity waveprint which the device obtains when the user places the device to their lips. The device may then emit waves of one or more wavelengths (such as sonic, ultrasonic, visible light, infrared or radio frequency) at a frequency, multiple frequencies or varying frequencies into the user's oral cavity, and in the case of some frequencies, into the surrounding tissues and, using one or more receptive sensors, measure the reflected characteristics of the wave and generate a composite oral cavity profile which can uniquely identify a user by virtue of the characteristics of the reflected waveforms, thereby authenticating the user as soon as the user puts the device to his or her lips, thus automatically unlocking the device to authorize a dose in a single seamless action from the user's perspective.

The server 208 may assimilate information from the devices 204, 210, and process the information for purposes of controlling the devices and generating reports. The reports may be designed to serve the needs of law enforcement, regulatory authorities, insurance companies, and other relevant authorities that are seeking to monitor the distribution of drugs, identify abuses, and are tasked with intervening.

In accordance with one aspect of the present application, the processing and analyzing of information may be performed partly or completely by the various node devices 204 (which in this embodiment, comprise drug dispensing devices), and node devices 210.

Figure 12:
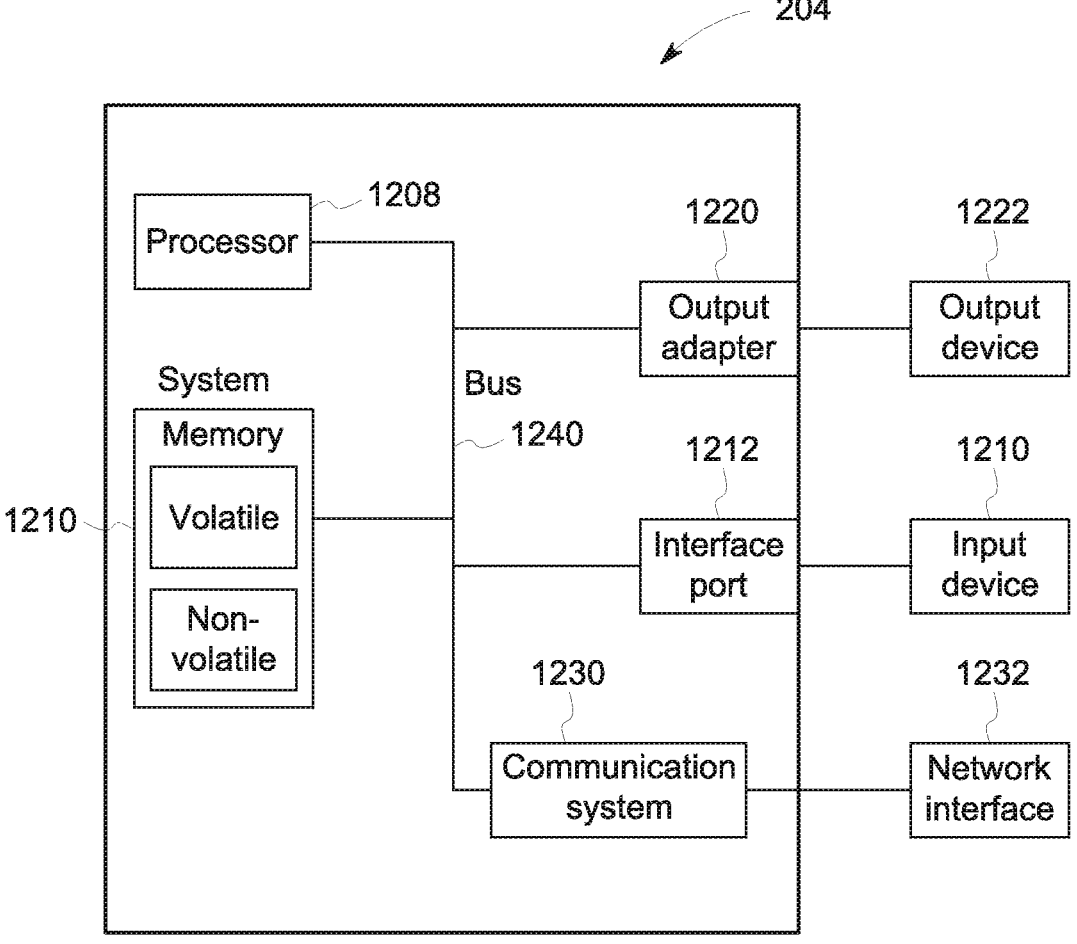
FIG. 12 is a block diagram depicting the circuitry of one embodiment of a dispensing device for use in the present application.

Referring to FIG. 12, the devices 204 therefore include electronic circuitry that includes a processor 1208, which may be configured to execute computer executable components stored in a memory 1210. The computer executable components can include a data input component, processing component and output component to create a block in a blockchain. Data for the block may include transaction records which record authentication or dispensing actions, or data obtained from sensors that are in or on a device 204, or are in communication with the device 204 (e.g. input devices 1210, such as a separate blood pressure monitoring cuff that is in Bluetooth communication with the device 204 through an input port 1212), or master data such as a dispensing schedule, or configuration data such as a validation table, or system data such as program code to run the system. The data for the blocks may also include time stamp information based on a system clock forming part of the circuitry of the device 204.

In one embodiment, one of the sensors providing input data is a fingerprint scanner to verify the identity of the user to ensure that only authorized users can dispense materials (in this case drugs) from the device 204. Based on the positive verification of the user, the processor 1208 can send a signal via an output adaptor 1220 to a valve or device activator or other control mechanism to control the dispensing of material. The control mechanism can thus control the dispensing of material from an output device 1222, such as a piezo ejector. After dispensing of material, the transaction is recorded on the blockchain.

As shown in FIG. 12, the circuitry of the device 204 also includes communications circuitry 1230 that is connected to the processor 1208 and a network interface 1232 via a system bus 1240, thus connecting the device 106 to one or more networks to facilitate communications with other devices 106 and the server 104.

As is discussed in greater detail below, the blockchain can thus be made up of blocks based on data received from multiple dispensing devices 106 (which define the nodes of the network). The system, in order to record data, first decides what block of data to write, then creates a hash from the previous block, includes it in the header of the current block, and thus creates a chain which, over time, links all previous blocks to the current block by virtue of the cascading hashing process. The header can further be comprised of a time stamp representing when the data was collected or uploaded to a public ledger. The header can also include an identifier to identify the source of the data, and a first hash based on the data.

The blockchain system can make use of hardware or software to capture data, authenticate the users of the dispensing devices, and perform big data analysis to identify patterns in the data and anomalies in the patterns. These anomalies may relate to the geographic location of a dispensing device, or the manner in which a user uses the device.

The processor 1208 can be comprised of multiple processing units, such as a central processing unit, a graphical processor, and other commonly-combined processing components, and can include hardware and software (e.g., a set of cores, a set of processes, software in execution, and similar components) to perform a computing task as discussed above. For example, the processor 1208 can execute data analysis algorithms which cannot be performed by a human. Depending on the nature of the interconnected node devices, the data can be raw data (e.g., raw audio, video, text, or numerical data, etc.) or data in compressed or uncompressed form captured by one or more sensors associated with the dispensing devices.

In a conventional blockchain as envisioned by Bitcoin and EOS, each device would have a copy of the blockchain. Information held on a blockchain exists as a shared, and continually reconciled, ledger, the ledger being a narrow and rudimentary implementation of a database. Thus, the blockchain isn't stored in any single location, allowing the records it keeps to be public and easily verifiable. No single centralized version of this information therefore exists for a hacker to corrupt. Instead, because the blockchain is hosted by thousands or millions of computers simultaneously, its data is accessible to anyone on the internet.

Consider the blockchain 300 shown in FIG. 3. This blockchain 300 is one embodiment of a blockchain located locally on a node device 106 and the server 108. All of the participating node devices 106 similarly include a similar copy if the same blockchain and can communicate and exchange information with the other nodes on the peer-to-peer network, and with the central server. These devices can each retain a copy of the most recent version of the block-chain. Furthermore, each node device is not merely a processing node but a dispensing device that generates new data. Thus, it also captures local data and may process it locally. It can then publish the raw or processed data as a transaction for adding to the blockchain as a new block or part of a new block. Once validated, each node device adds the new block to its copy of the blockchain.

Figure 13:
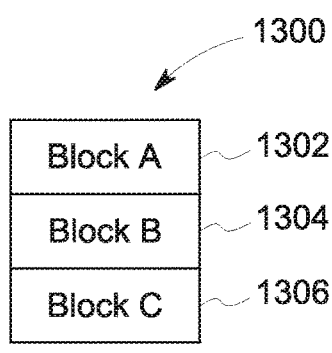
FIG. 13 is a simple depiction of one embodiment of a blockchain design.

In the above implementation of a blockchain system, the server 208, like the devices 204, includes memory. The server memory is configured to include a database, which, in addition to containing master, transaction, configuration and system data in non-blockchain form, also can contain one or more copies of the blockchain, and can perform additional analysis and generate reports for internal use or for use by third parties. The database can store the data or some of the data in block form, such as depicted by blocks 1302, 1304, 1304 in FIG. 13, with headers and data areas, thus defining a copy of the blockchain.

Figure 14:
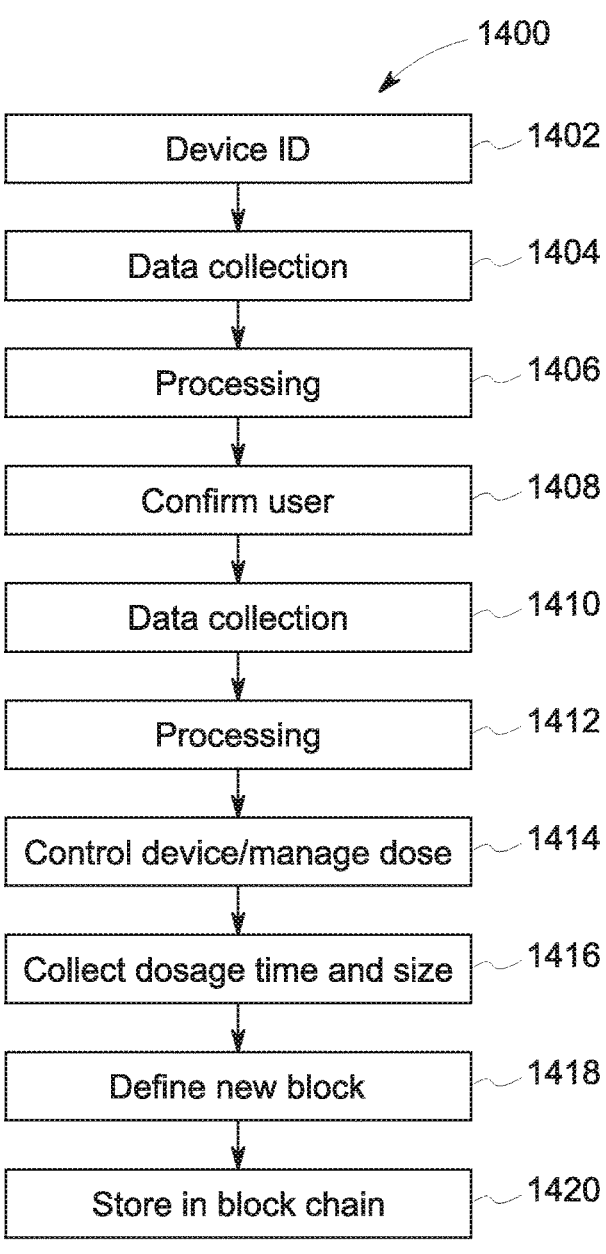
FIG. 14 is a flowchart showing one implementation of the logic associated with the creation of new blocks by dispensing devices forming part of one embodiment of the present application.

FIG. 14 shows a flow chart of one embodiment of a computer-implemented method of the present application.

Considering just one copy of the blockchain: blocks in the Blockchain are linked by virtue of a hash of the previous block. To link two blocks together, the preceding block is hashed. The hash is a compact digest and a nearly-unique number, which acts as a surrogate identifier for the data in that block, and the subsequent block will be linked to the preceding block by including the hash of the preceding block within the header of the subsequent block. This permits subsequent validation of continuity and integrity of the blockchain by other nodes or processes after the block has been written and distributed to other nodes or to the central server.

As shown in FIG. 14, the device identification information 1400 is collected at step 1402 to define the start of a new transaction, which can, in one implementation, be written into a new block. As subsequent blocks are created, they are linked to the previous blocks. A timestamp is included in the header to identify the order in which the blocks were received.

A device may accumulate one or more records of information and perform analysis before writing it into a new block. In the embodiment of FIG. 14, data is collected to validate the identity of the user of the device (step 1404). This may take the form of capturing a fingerprint scan, voiceprint, iris scan, or any biometric measurement which can help to identify a user. In step 1406 this information is processed by comparing the information to previously downloaded data or by transmitting the data to one or more network nodes or to the central server for analysis and verification. If the user's identity is validated by comparing it to a list of valid users for the device—that list being possibly stored on the blockchain—then the user is confirmed (step 1408) and may operate the device.

Steps 1404 through 1408 can occur before 1402, or they can occur simultaneously.

Another set of data is collected in this embodiment (step 1410). This may include the time the user tries to activate the device, the user's location, and any physician or authorized third party overrides that may force a deviation from a pre-programmed dispensing regimen. The information is processed in step 1412 and the results used to control the device to either activate or de-activate it, and potentially to decide upon or alter the quantity of dispensed material, and optionally generate a feedback message to the user.

If dispensing has not been denied, and once an amount and quantity of material has been dispensed, the dispensing time and quantity is collected (step 1416) and then submitted as one or more new records (step 1418) to define a new block to be added to the blockchain (step 1420). This can include the generation of a hash by the processor 1208. By performing a bashing function, the processor 1208 generates a number that represents the data in the block. As discussed above, the data processing can include user authentication, based on a comparison of previously stored data and data received from a dispensing device. It may also include analysis to identify anomalies in the incoming data, e.g. analysis of geolocation data, or analysis of biometrics data about the user of the dispensing device, or other data.

Figure 15:
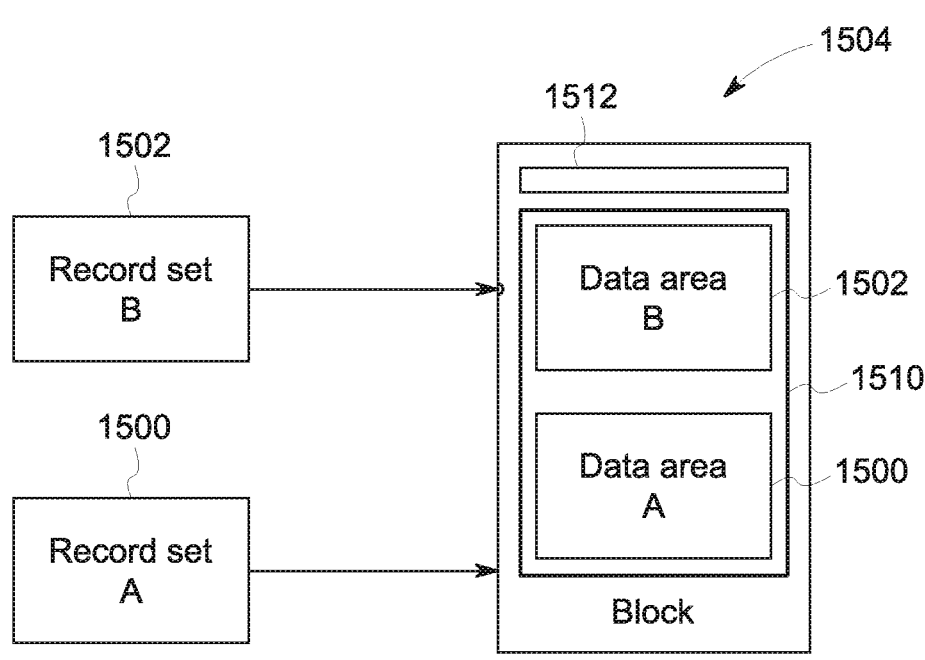
FIG. 15 depicts one embodiment of the process of block formation for a blockchain.

FIG. 15 shows a block diagram of a one embodiment of a blockchain formed from sets of data from multiple sources. The blockchain system (e.g., blockchain system 200), when collecting data (as described in steps 1404 and 1410 above) can capture data from separate data sources such as data from a first dispensing device (data records 1500), and data from a second dispensing device (data records 1502).

The record sets 1500, 1502 from the two devices can be formed into one or more blocks having a data area 1510 and a header 1512, wherein the header is comprised of device JDs associated with the dispensing devices. As mentioned above, one or more of the record sets can be added to separate blocks of the blockchain, or the records can be combined into a single block 1504, as shown in FIG. 15, which is then hashed.

In some embodiments, the data in one or more of record sets 1500, 1502 may be encrypted, while in other embodiments, only the header in block 1504 may be encrypted while the data area of the block is unencrypted, or in other embodiments, the data area may be encrypted and the header is not.

Data that is included in a block can be in the form of records of any single type or combination of types including but not limited to transaction, master, configuration, system and analytic data. Thus, for example, a block may include both transaction and analysis data or the analysis data may be added to as separate blocks to the blockchain.

Figure 4:
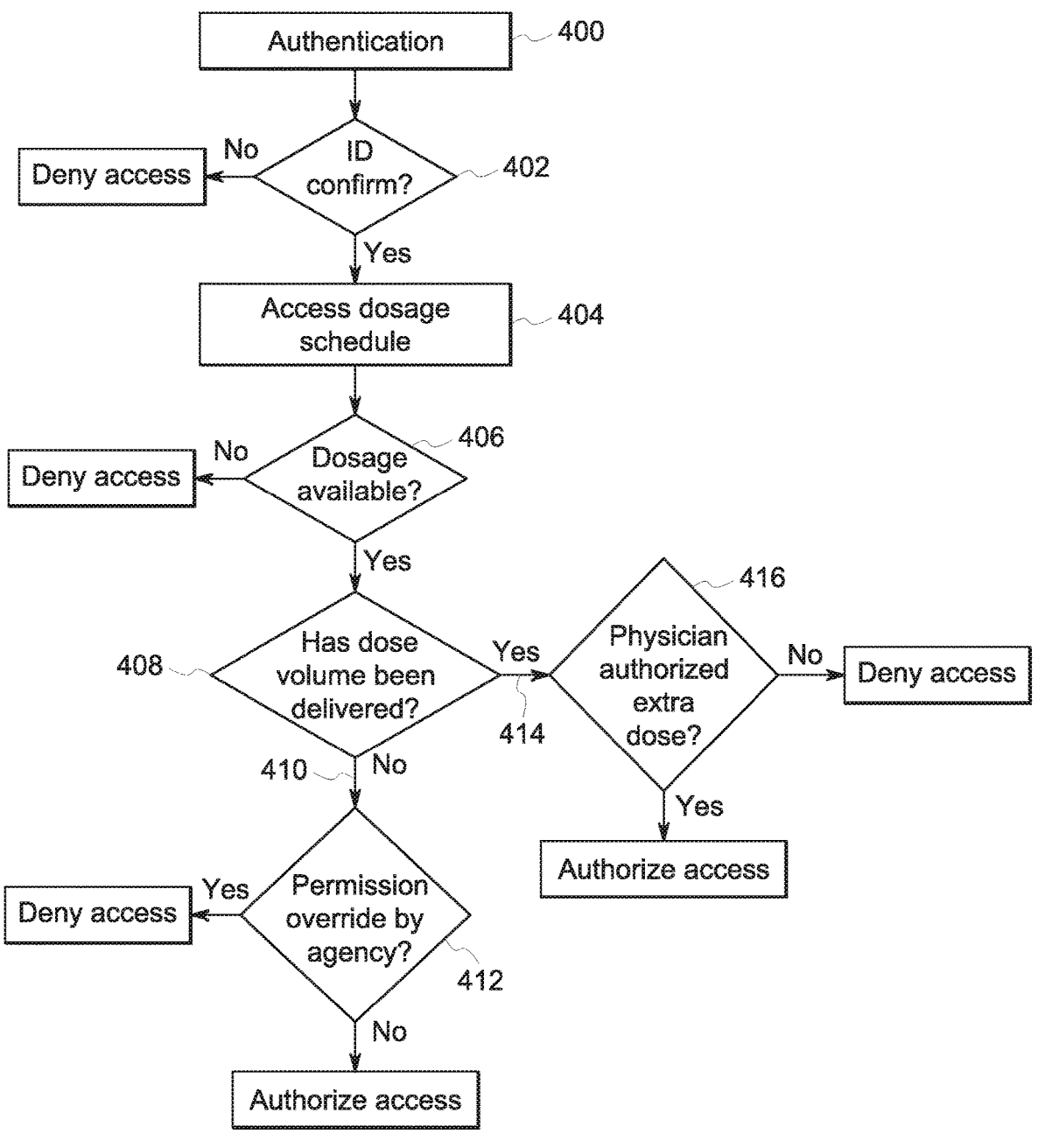
FIG. 4 is a flow chart defining the logic of another embodiment of user authentication and dispensing authorization.

As discussed with reference to FIG. 4, processing or analysis 406, 412 may be performed on the data previously collected. Referring to FIG. 15, the blockchain system can, in one embodiment, insert record sets 1500, 1502 into the blockchain as a combined block 1504, wherein the record sets include both transaction and analysis data.

Figure 16:
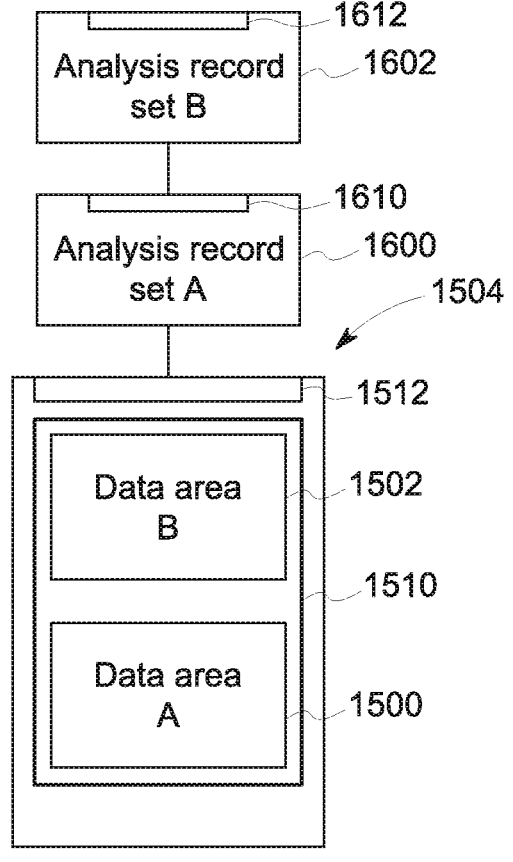
FIG. 16 depicts one embodiment of a simple blockchain of blocks containing transaction data and analytic blocks.

In another embodiment the analysis data is added to the blockchain as one or more separate blocks. Referring to FIG. 16, the analysis record sets 1600 and 1602, which may be the result of various processing steps or computation algorithms performed on the transaction data, are added to the blockchain as separate blocks in this embodiment.

Apart from the block headers, one or more of the record sets, e.g., analysis record sets 1600, 1602, can have additional headers 1610, 1612 that include various types of information, e.g., relating to the source of the data, or the identity of the user, or time stamp information, or any data that applies to all records in the set, and each record can contain a hash of that record. The record sets can be included into the chain in various ways, e.g., record sets 1600, 1602 can be inserted into separate, data areas 1502, 1500 within block 1504, as shown in FIG. 16, or the blockchain may be linear, where blocks are added as they are created. For instance, transaction data is collected first and a transaction data block is created, whereafter an analysis block is added linearly to the blockchain. In such an embodiment, analysis record set 1600 can be included into a data block containing data area 1500, and analysis record set 1602 can be included into a separate block containing the data area 1502.

In other embodiments, the blockchain can exist as many simultaneous parallel chains, or as a single chain which bifurcates and optionally recombines as processing is performed and documented on different datasets and data sources where the data sets are gathered at different times in varying locations from multiple devices.

Figure 17:
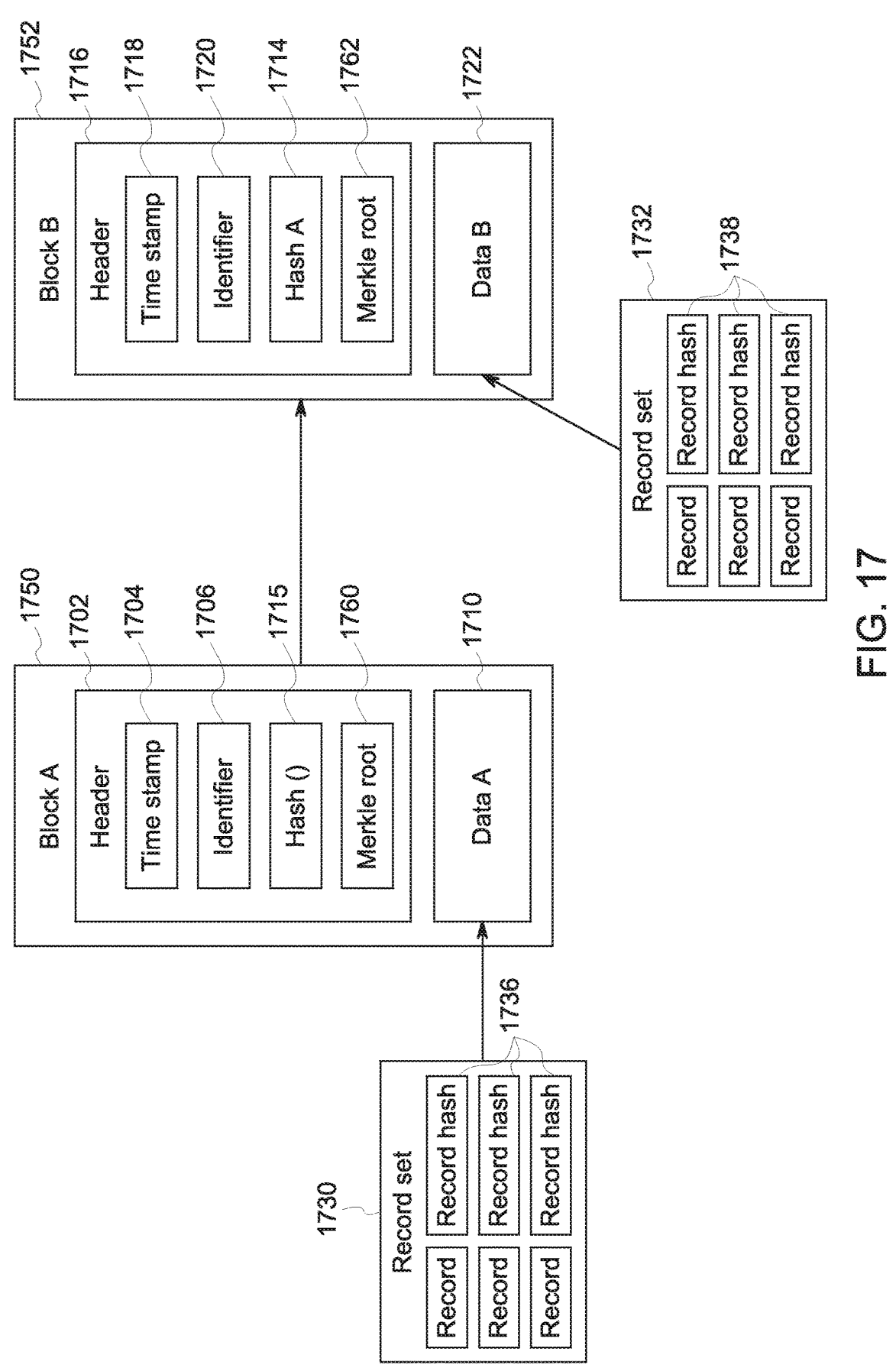
FIG. 17 shows a block diagram of one embodiment of block structures and link formation in a blockchain of the present application.

One embodiment of the structure of two successive blocks, and the way they are linked together, is shown in FIG. 17, which depicts the linking of any two blocks 1750, 1752 such as the linking of block 1504 of FIG. 15 to a previous block.

In this embodiment, each data area 1710, 1722 contains one or more record sets 1730, 1732 (usually transactions, but can instead or also contain master, configuration, system or analytic data) and each record in set 1730, 1732 is followed by a record hash field 1736, 1738, which contains the hash value of each associated record, which may be created using the same or different hashing algorithms.

In one embodiment, one or more of blocks 1750, 1752 can include a header 1702, 1716, respectively, as well as a data area 1710, 1722, respectively. The headers 1702, 1716 can include information identifying the user and/or device (identifiers 1706 and 1720). Blocks 1750, 1752 can also include timestamps 1704, 1718 that may identify the time that the blocks were formed on a node or central server, or the time when the sets of data in data areas 1710 and 1716 were received by the node or central server. The headers 1702, 1716 can also contain one or more Merkle Root fields 1760, 1762, one or more of which will contain a hash of all the hashes 1736, 1738 of the records contained within the data area of the current block. This serves the purpose of another node being able to perform a higher-speed validation of the chain without having to download the data areas of all or any blocks, since the Merkle root adequately represents the records in the data area in absentia. Having multiple Merkle Roots using differing hashing algorithms also greatly increases the difficulty a would-be attacker would face if attempting to brute-force a differing set of transactions and arrive at the same Merkle Root in order to falsify transactions on the chain.

Block 1752 can also include a hash 1714 (a number of a predefined length that is the output from a hash function operating on the data in data area 1710, or on some or all the information which comprises block 1750, including the header 1702. The hash 1714 is a number that is the output of a mathematical hashing function, which uses as input part or all of the header and data in block 1750, such that any modification to block 1750 will result in a different hash output value that is different from the original.

The hashing function is chosen to have sufficient complexity and characteristics such that a would-be attacker is would be unlikely to be able to create a block, using current technology, having a different set of data and yet still arrive at the same hash value 1714.

The hash 1714 of data block 1750 can be included in the header of subsequent block 1752. By adding the hash 1714 to block 1752, a link is created between the two data blocks, and thus the blockchain is formed. Any modifications to the data area or any other portion of block 1750 would result in the output from the hash function not matching the value stored in field 1714 of block 1752, and the corruption would be detected by any node which received the two blocks and the corrupted block 504 would be rejected by all nodes on the network.

In another embodiment, there may be multiple hashing functions whose output is written to block 1752 into multiple hash fields similar to 1714 this being useful to greatly increase the level of difficulty needed to generate a new set of transactions which when hashed generate the same hash value as that stored in the header of block 1752.

Just as Block 1752 has a hash of the data in block 1750, so block 1750 will have a hash 1715 of the data in the preceding block in the chain (not shown). Even the very first block in the chain—called the Genesis block—has a hash field. The first block will have a dummy "seed" value because there is no previous block, and the code will have a special case coded into it to handle the first block. In various embodiments, the headers 1702 and 1716 or record sets in data areas 1710 and 1722 may also include URLs linking to data in one or more public or non-public databases or ledgers, e.g., for making reports available to certain authorities. Thus, the server 108, which will maintain a copy of the blockchain, will automatically be able to generate reports to the relevant authorities.

The headers 1702 and 1716 or the data areas 1710 and 1722, or both the headers and the data areas may be encrypted to protect sensitive information.

The computer-implemented methods described in this application are depicted and described as a series of steps. It is to be understood and appreciated that the subject innovation is not limited by the steps illustrated and/or by the order of steps, for example steps can occur in various orders and/or concurrently, and with other steps not presented and described herein. Furthermore, not all illustrated steps are required to implement the computer-implemented methods in accordance with the application. Also, those skilled in the art will appreciate that the computer-implemented methods could alternatively be represented as a series of interrelated states via, a state diagram or events. Additionally, it should be further appreciated that the computer-implemented methods disclosed hereinafter are capable of being stored on an article of manufacture to facilitate transporting and transferring such computer-implemented methods to computers. The term article of manufacture, as used herein, is intended to encompass a computer program accessible from any computer-readable device or storage media.

Moreover, because the configuration of data packets and communication between processors and an assignment component is established from a combination of electrical and mechanical components and circuitry, a human (or non-human) is unable to replicate or perform the subject data packet configuration or the subject communication between processors and an assignment component. For example, a human is unable to generate data for transmission over a wired network or a wireless network between processors and an assignment component, etc. Moreover, a human is unable to packetize data that can include a sequence of bits corresponding to information generated during a machine learning process (e.g., a blockchain formation process), or transmit data that can includes a sequence of bits corresponding to information generated during a machine learning process.

Figure 18:
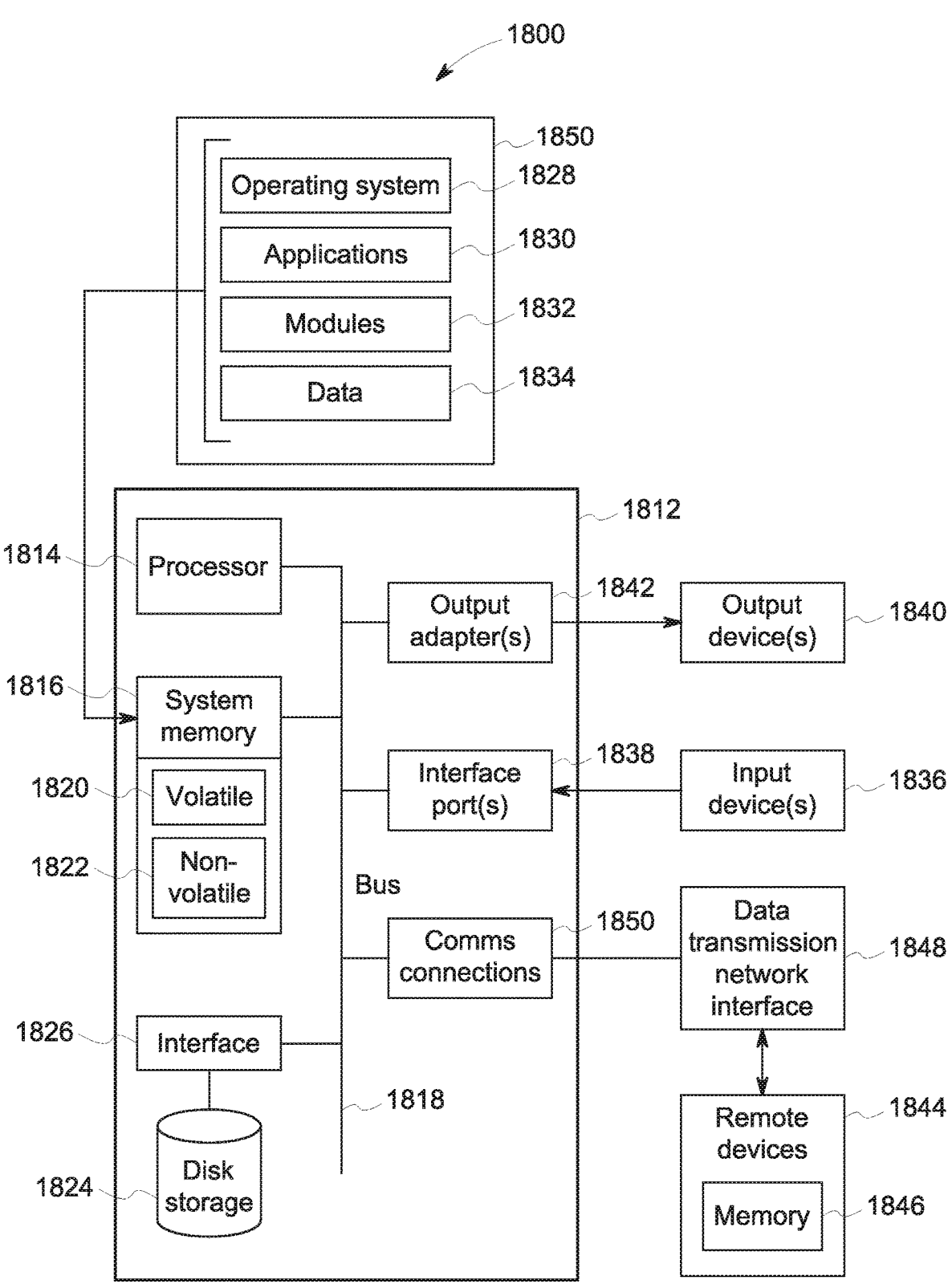
FIG. 18 is a block diagram depicting the circuitry of one embodiment of a central server for use in the present application.

In order to provide a context for the various aspects of the disclosed subject matter, FIG. 18 as well as the following discussion are intended to provide a general description of a suitable environment in which the various aspects of the disclosed subject matter can be implemented.

FIG. 18 shows a suitable system or operating environment 1800 for implementing various aspects of the present application. The system includes a central server or computer 1812 (such as server 208 discussed with reference to FIG. 2), which includes a processor 1814, a system memory 1816, and a system bus 1818. The system bus 1818 connects system components including, but not limited to, the system memory 1816 to the processor 1814. The processor 1814 can include dual microprocessors and other multiprocessor configurations. The system bus 1818 can be any of several types of bus structure(s) including a memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI). The system memory 1816 can be implemented as a volatile memory 1820 or nonvolatile memory 1822. The basic input/output system (BIOS), containing the basic routines to transfer information between elements within the computer 1812, such as during start-up, is stored in nonvolatile memory 1822, which can include read only memory (ROM), programmable ROM (FRONT), electrically programmable ROM (EPROM), electrically erasable programmable ROM (EEPROM), flash memory, or nonvolatile random access memory (RAM) (e.g. ferroelectric RAM (FeRAM). Volatile memory 1820 can include random access memory (RA M), which acts as external cache memory. e.g., static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM) direct Rambus RAM (DR-RAM), direct Rambus dynamic RAM (DRDRAM), and Rambus dynamic RAM.

The computer 1812 can also include storage media of any type currently known or to be invented in the future. FIG. 18 illustrates, for example, a disk storage 18241 which can include devices like a magnetic disk drive, floppy disk drive, tape drive, Jaz drive, Zip drive, LS-100 drive, flash memory card, memory stick or DNA-based storage systems. The disk storage 1824 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1824 to the system bus 1818, a removable or non-removable interface is typically used, such as interface 1826.

Also depicted in FIG. 18 is the software 1850 that acts as an intermediary between users and the basic computer resources forming part of the operating environment 1800. The software can include an operating system 1828, which can be stored on disk storage 1824, and serves to control and allocate resources of the computer 1812.

Commands or information are entered into the computer 1812 through input device(s) 1836, including pointing devices such as a touch-screen, mouse, trackball, stylus, touch pad, keyboard, microphone, joystick, game pad, satellite dish, scanner, TV tuner card, digital camera, digital video camera, web camera, and the like. These and other input devices connect to the processor 1814 through the system bus 1818 via interface port(s) 1838, which include, one or more of, a serial port, a parallel port, a game port, a universal serial bus (USB), or other communication protocol such as thunderbolt, firewire, or a proprietary protocol.

Output device(s) 1840 may use the same type of ports as input device(s) 1836. Thus, for example, a USB port can be used to provide input to computer 1812, and to output information from computer 1812 to an output device 1840. Output adapter 1842 is provided to illustrate that there are some output devices 1840 like monitors, speakers, and printers, among other output devices 1840, which require special adapters such as video and sound cards that provide a means of connection between the output device 1840 and the system bus 1818.

Computer 1812 can operate in a networked environment using logical connections to one or more remote computers, such as remote computer(s) 1844. The remote computers 1844 can be node devices like the dispensing devices 204, discussed above, or can be comprised of other computers, servers, routers, network PCs, workstations, microprocessor based appliances, peer devices such as a material dispensing devices, which can include some or all of the elements described in relation to computer 1812.

Remote computers 1844 are logically connected to computer 1812 through a data transmission interface 1848 such as any network protocol, Wi-Fi, Bluetooth, nearfield or any other data transmission protocol and physically via communication connection 1850. Data transmission interface 1848 can include either wire or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include point-to-point links, circuit switching networks like integrated Services Digital Networks (ISDN) and variations thereon, packet switching networks, and Digital Subscriber Lines (DSL). Wi-Fi, Bluetooth, nearfield or any other data transmission protocol.

Communication connection 1850 refers to the hardware and/or software employed to connect the data transmission interface 1848 to the system bus 1818. While communication connection 1850 is shown for illustrative clarity inside computer 1812, it can also be external to computer 1812. The hardware/software for connection to the network interface 1848 can also include internal and external technologies such as, modems including regular telephone grade modems, cable modems and DSL modems, ISDN adapters, and Ethernet cards.

Some of the above embodiments define a server, which in FIG. 1 was depicted as server 104. While a centralized server may be used to implement some of the processing and report generation, the present application is not so limited.

As was discussed above, a blockchain platform, and particularly the server functionality, may be implemented in any computing environment or configuration such as cloud, onsite or hybrid which includes one or more compute nodes with which local computing devices (e.g. material dispensing devices) communicate, or that are themselves defined by such local computing devices. The compute nodes, in other embodiments may include devices such as personal digital assistants (PDAs) or cellular telephones, desktop computers, laptop computers, and automobile computer systems. Nodes may communicate with one another in peer-to-peer configuration. They may be grouped physically or virtually, in one or more networks, such as Private, Community, Public, or Hybrid clouds as discussed above, or a combination thereof. This allows the computing and networked environment to offer infrastructure, platforms and/or software as services for which a data consumer. e.g., a dispensing device does not need to maintain a full set of resources on a local computing device.

The present invention includes a system for managing devices and dispensing material. It also includes a method for implementing such a system, and a computer program product that is comprised of a computer readable storage medium (or media) having computer readable program instructions thereon for causing a processor to carry out aspects of the present invention.

The computer readable storage medium can be a tangible device that can retain and store instructions for use by a processor or other an instruction execution device. The computer readable storage medium includes any one or more of, an electronic storage device, a magnetic storage device, an optical storage device, an electromagnetic storage device, a semiconductor storage device, or any suitable combination of the foregoing. A non-exhaustive list of more specific examples of the computer readable storage medium also includes a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM, a digital versatile disk (DVD), a memory stick, a floppy disk, etc. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

The computer readable program instructions can be downloaded to a computer or other processing device via a network, for example, the Internet, a local area network, a wide area network, or any wireless network. The network can comprise copper transmission cables, optical transmission fibers, wireless, optical, infrared, sonic or ultrasonic transmission, routers, firewalls, switches, gateway computers and/or edge servers. A network adapter card or network interface in each computer receives computer readable program instructions from the network and forwards the computer readable program instructions for storage to a computer readable storage medium connected to the computer.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages.

As discussed, the present invention is preferably implemented as a distributed system with at least some processing taking place at the various nodes (e.g. a user's computer, smart phone, or dispensing device). The computer readable program instructions can thus be executed entirely on the local node (e.g. user's computer, smart phone, or dispensing device) partly on the local node and partly on a remote node, or entirely on a remote node such as a server. The remote node forms part of the network and can be connected to the users' node(s) through any type of data transmission scheme and protocol, including a local area network (LAN) or a wide area network (WAN), or the connection can be made to an external node (for example, through the Internet using an Internet Service Provider).

In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

The present invention is described with reference to flowcharts and block diagrams to help explain the methods, system, and computer program products of the invention. It will be appreciated that each block of the flowchart and block diagrams can be implemented by computer readable program instructions, which can be provided to a processor of a general purpose computer, special purpose computer, or other programmable apparatus to produce a machine, such that the instructions, when executed by the processor, implement the functions or steps specified in the flowchart or block diagram. The computer readable program instructions can also be stored in a computer readable storage medium to direct a processor to function in a particular manner. The computer readable storage medium with the instructions stored thereon, thus comprises an article of manufacture including instructions which implement aspects of the flowchart or block diagram.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s).

In some implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

One aspect of the present invention involves distributed processing. Each block of the block diagrams or flowchart, can therefore be implemented by special purpose hardware-based systems, e.g. implemented in each of the dispensing devices (acting as nodes or local processing devices), to perform specified functions or acts making use of special purpose hardware or software instructions. In such a distributed computing environment where at least some of the tasks are performed by remote processing devices, the devices are linked through a communications network, and program modules can be located in both local and remote memory storage devices.

Those skilled in the art will appreciate that the inventive computer-implemented methods can be practiced using a wide variety of computer system configurations, including single-processor or multiprocessor computer systems, mini-computing devices, mainframe computers, hand-held computing devices (e.g., smart phones), microprocessor-based or programmable consumer or industrial electronics, etc.

As used in this application, the terms "component," "system," "platform," "interface." and the like, can refer to, or can include, a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. Components can also execute from various computer readable media having various data structures stored thereon. The components can communicate via local or remote processes. e.g., by transmitting a signal having one or more data packets, allowing data from one component to interact with another component in a local system, distributed system, or across a network such as the Internet.

In the case of a dispensing device for dispensing liquid or solid material, a component can be an apparatus with specific functionality as defined by its mechanical parts and controlled by electronic circuitry with software or firmware application executed by a processor. In such a case, the processor can be internal or external to the apparatus and can execute at least a part of the software or firmware application.

As it is employed in the subject specification, the term "processor" can refer to substantially any computing processor or device comprising, but not limited to, single-core processors; single-processors with software multithread execution capability; multi-core processors; multi-core processors with software multithread execution capability; multi-core processors with hardware multithread technology: parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processors. In this disclosure, terms such as "store." "storage," "data store," data storage," "database," and substantially any other information storage component relevant to operation and functionality of a component are utilized to refer to "memory components." entities embodied in a "memory." or components comprising a memory. It is to be appreciated that memory and/or memory components described herein can be either volatile memory or nonvolatile memory, or can include both volatile and nonvolatile memory. For example, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory. The term RAM shall include any of its forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DR DRAM), and Rambus dynamic RAM (RDRAM).

In addition to securing transactions and communications from and to dispensing devices by means of a blockchain, one of the aspects of the present invention is to avert physical abuse of the dispensing devices and their contents.

To avoid the physical tampering with a dispensing device in order to bypass the dispensing mechanism and obtain the substance without being subject to device controls, several safeguards are envisioned by the present invention. One safeguard, discussed above, is the inclusion of a secondary housing containing a neutralizing or immobilizing agent or substance that surrounds the dispensed substance, and serves to mix or interact with the substance and reduce or eliminate the desirability, the value, or usability of the substance if the dispensing device is tampered with. In another embodiment, instead of a chemical agent, an energetic force such as vaporizing heat, evaporative plasma, or EMF (in the case of a ferro-magnetic substance) may be applied to the substance which could permanently or temporarily alter it quickly enough to render it unobtainable, undesirable or unusable.

Figure 19:
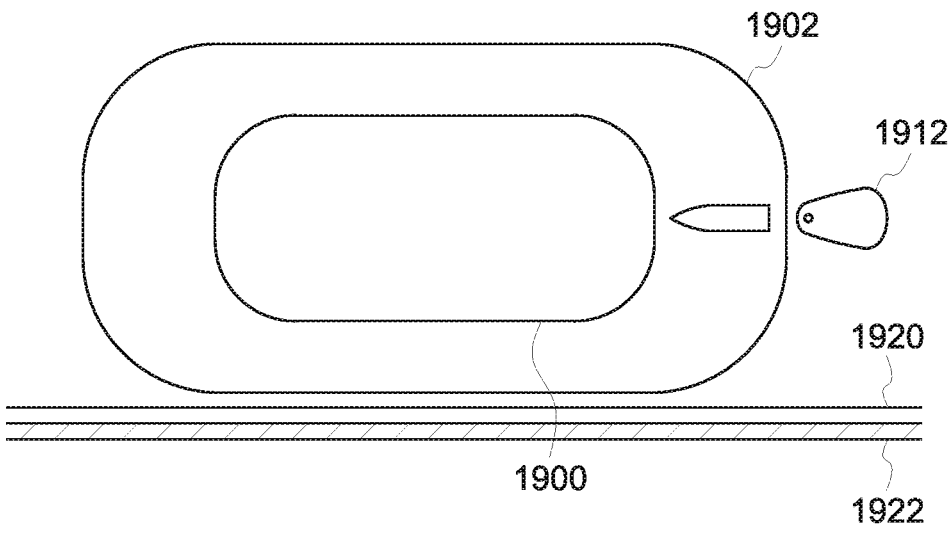
FIG. 19 is a sectional side view of one embodiment of a substance-containing housing and neutralizing agent-containing housing of the invention.

In one embodiment, shown in FIG. 19, the substance-containing housing 1900 may comprise a bladder or rupturable section, wherein the housing 1900 is surrounded by a neutralizing-agent-containing housing 1902, which may take the form of a second bladder, wherein lances 1904 or other impaling devices are aligned with the substance bladder or rupturable section and configured to provide flow communication between the neutralizing agent-containing housing 1902 and the substance-containing housing 1900 if the device is tampered with. The rupturing of the substance-containing housing may be triggered by sensors 1920, e.g., strain gauges or open circuit detectors (such as conducting wires) embedded or mounted in the walls 1922 of the dispensing device, which initiate the rupturing process. This may, for example involve an electrical motor-driven piston or cam 1912 that pushes a lance through the intervening walls of the substance-containing housing 1900 and neutralizing-agent-containing housing 1902.

Figure 20:
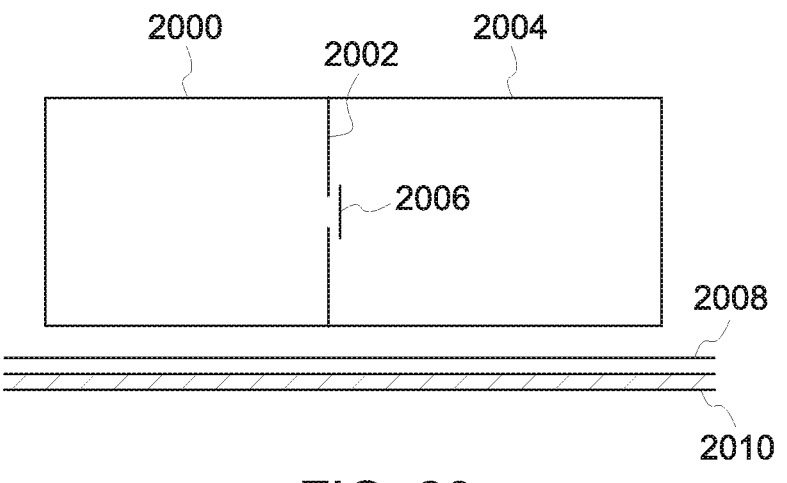
FIG. 20 is a sectional side view of another embodiment of a substance-containing housing and neutralizing agent-containing housing of the invention.

In another embodiment, shown in FIG. 20, the substance-containing housing 2000 may share a wall 2002 or may by connected by a tube with a neutralizing-agent-containing housing 2004, wherein the intervening wall 2002 or tube includes a valve 2006 that is triggered by one or more sensors in the dispensing device, e.g. strain gauges or open circuit sensors 2008 mounted in the wall 2010 of the dispensing device, so as to trigger the valve 2006 in the event of a breach or other tampering with the device wall. The valve 2006, once triggered, allows antagonist to flow through to the substance-containing housing 2000.

As discussed above, the blockchain may be configured to control the dispensing of quantities of substance by the various devices, and can shut down a device in the event of suspicious behavior, e.g., if the device is moved outside of a designated geographic region or if the device is tampered with. Since some users may attempt to circumvent such security measures, e.g., by blocking communications signals by wrapping the device in aluminum foil, one implementation of the system involves monitoring correct use of the devices. Thus, for example, user compliance can be monitored for a device by having the device transmit a confirmation signal each time a dose is delivered, which may be in the form of a record written to the blockchain and the block transmitted to the network. Failure to communicate such compliance information results in the device being flagged to allow a responsible entity such as a physician to follow up to ensure that a substance recipient such as a patient remains compliant, or to ensure that the device is functioning correctly. It also allows the device to be remotely inactivated or allows responsible entities such as legal authorities to intervene if a device's communications system is being or suspected of being interfered with.

Figure 21:
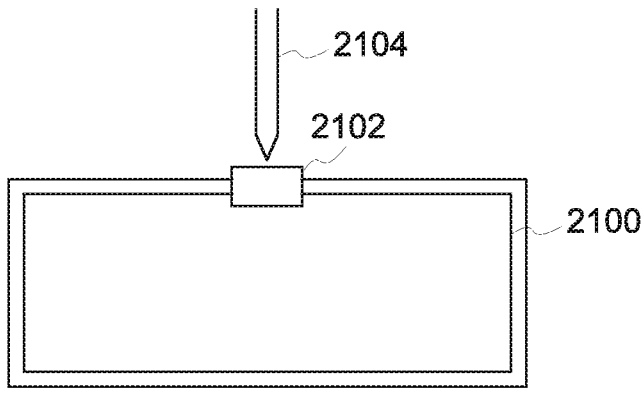
FIG. 21 is a sectional side view depicting one method of replenishing the substance in a device.

Apart from monitoring compliance with a dispensing scenario such as a patient dosing regimen, the system may be configured to have a device send a notification or alarm signal if it is tampered with (e.g. sensors in the device wall detect a breach or excessive pressure variation, indicative of tampering) directly over the network or via data written to the blockchain or both, or if the device fails to communicate for a pre-defined period of time. In the latter case, the processors in the devices may be programmed to send an "All is well" type of signal at certain intervals e.g., once every 12 hours and if these are not received, the system may issue an alarm to authorized personnel, flagging the device in question to resolve the discrepancy. A filling station or replenishment device was also discussed with respect to FIG. 2 above. This may be used e.g., at a pharmacy, to re-fill a depleted drug reservoir on a dispensing device. In one embodiment, shown in FIG. 21, the dispensing device may have a reservoir 2100 with a self-sealing rubber inlet port 2102 that can be pierced by a hypodermic needle 2104 on the filling station to refill the reservoir 2100.

Figure 22:
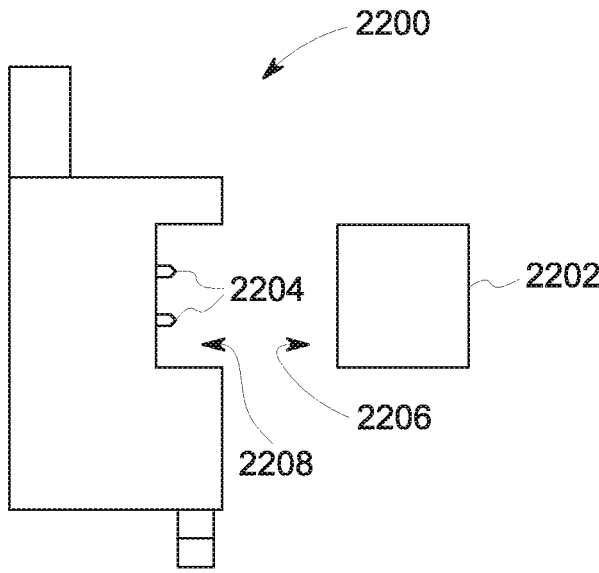
FIG. 22 shows a side view of one embodiment of a delivery device making use of a replaceable substance-containing cartridge.

In another embodiment (FIG. 22), the dispensing device 2200 is configured to receive replaceable cartridges 2202, pre-filled with the desired material, e.g., an opioid. The device 2200, in this embodiment, includes a set of hypodermic needles 2204 to rupture a membrane 2206 on the cartridge 2202 when the cartridge is slotted into the complementary housing 2208 in the device 2200, thereby allowing the drug to flow into the dispensing mechanism of the device. In one embodiment, in which a piezo ejector is used to particularize or aerosolize a liquid material, the cartridge may include both a reservoir for the substance and the piezo ejector with its mesh plate, thereby ensuring that a fresh mesh plate is used with each replenishment of the device 2200.

The supporting blockchain infrastructure may contain— either on the previously-discussed chain, or on a separate chain, a blockchain whose purpose is to record a chain-of-custody for the device, or any components of the device, or the contents of the device. For each change which occurs to the device, any component of the device, or any content of the device, the change will cause a transaction record to be written to the chain-of-custody blockchain or portion of the blockchain so as to forge a reliable and indelible history of who has changed or adjusted the device, components or contents, what change occurred and when.

In one embodiment, the dispensing device may be fitted with a sensor to detect the quantity of substance remaining in the chamber, using a sensor such as an ultrasonic transducer and receiver whereby transmitting waves into the cavity generates and returns a signal which can be interpreted to determine the substance volume, or substance-to-air ratio. In another embodiment, the chamber itself may be fitted with the sensor, such as a conductive strip, or resistive strip or casing whose resistance or conductance or other measurable property changes in proportion to the amount of contained substance. These are useful to physically determine the amount of remaining substance and thereby act as an audit mechanism for the correct function of the device, dispensing count, and flow rate sensors. Keeping track of the remaining substance in a chamber or reservoir before and after delivering a dose or quantity also serves as a way of validating that the correct dosage or quantity was delivered, and if need be, dispense more substance to ensure compliance with the desired dose or quantity. After measurement, the result can also be used to correct the remaining stock level estimates provided by the other sensors. Since stock-taking and stock-level adjustments are a very expensive process in inventory management, these add quantifiable value and utility to the device.

In addition, any of the above components, component groups, sensors and controls and all combinations thereof mentioned in this document can be redundantly implemented in any combination and in any number of redundant combinations to provide additional veracity, integrity and reliable operation of a device.

Another important factor to consider is patient safety. This may include safeguards to prevent over-dosing or contraindications with other drugs or mental conditions.

Patient Safety and Biofeedback Mechanisms

It is well-known in the field medicine that there are visual, auditory and behavioral tests which may be performed to assess the physical and mental condition of a patient and infer the medical condition of a body or the presence of substances such as alcohol or methamphetamines, or the presence of pathological condition.

In order to avert harm to a patient, the device may be fitted with the ability to perform physical and psychometric testing before, during or after dispensing in order to, for example, detect the pre-existing presence of opioids before dispensing is permitted, or to detect the onset of neurotoxicity during a dosing regimen.

One way to detect the presence of medications or symptoms is by measuring pupil dilation. In order to measure pupil dilation, the device may take a picture of the pupil and analyze using software and produce a measurement of dilation, for example by measuring the outer and inner diameters of the iris and producing a ratio of diameters.

For this measurement, the ideal situation is that the patient would keep light levels the same, however the image analysis can also quantify the level of ambient light and light falling on the eye in order to compensate for changes in light levels on the eye.

A baseline date and time-stamped image may be used as a reference for measuring change in pupil size, and thus dilation.

In the event that a baseline un-dilated image is not available, another embodiment to determine if a pupil is dilated determines the pupil's change in size in response to changing light conditions. This may include taking two consecutive images, wherein a light is shone into the eye for the second image, for example by turning on the led on a cellphone camera and letting it remain on for a pre-defined period of time before taking the picture in order to permit the pupils time to respond to the brightness of the light. This will detect how much a pupil responds to the light. A pupil that doesn't change much or at all is considered to be dilated, because typically, dilated pupils don't respond normally to light. If the pupil is completely unresponsive to light it is called a "fixed" dilated pupil.

In a third alternative embodiment, or in addition to one of the above tests, two consecutive pictures are taken, with a bright light shining into the eyes first, then without the bright light. This measures the pupil's ability to recover from a bright light source. This effect can last two hours or longer after the ingestion of some drugs such as alcohol and marijuana, and would provide a good indication of their presence in the body. This is a useful test because these drugs by themselves do not cause the pupils to dilate.

Examples of drugs that by themselves cause the pupils to dilate are:

Amphetamines
Cocaine
LSD
MDMA (Ecstasy)

Having the patient perform a pupil test before a medication is permitted to be dispensed by the device may form a part of the logic the device uses to determine if a dose may be administered. Thus, it provides a safeguard to prevent harm to the patient through overdosing or due to complications from contraindicated medication. For example pupil tests may be used to test for indications of the presence of recreational drug use such as alcohol before dispensing a dose, and in the case where the medication may not be used or is dangerous to take with alcohol, the device would deny the dispensing of the dose in the interest of patient safety.

While most drugs tend to lead to dilation or enlarging of the pupils, in the case of opioids, it leads to pupil constriction. This constriction of pupils is a telltale sign of opiate use because it is so uncommon otherwise. If the tests measure a pupil constriction, this would indicate the possible presence of opiates in the system and the dispensing may not be approved, or the dose schedule or dose size may be temporarily modified in the interest of patient safety, with the goal to prevent complications and overdosing due to the pre-existing presence of opioids in the patient.

The pupil constriction test may also be performed afterward as an objective measure of the efficacy of a dose, and if the amount of constriction is small or non-existent, as may happen if the dose was not inhaled deeply, or expelled before adequate absorption (if the patient coughed), or in the case of opioid tolerance, the detection of non-constriction may be used as the basis for permitting the release of additional dose(s). This can be automated by making use of software logic to automatically adjust dosages based on pupil size measurements.

In yet another embodiment, tests which can be employed to indicate and measure the presence of medication in the patient involve having the patient stream video into the device while simultaneously reading out loud letters, words or describing displayed images, the words being received by a microphone on the device and the spoken words recognized and the response analyzed. These letters and images may have varying characteristics such as size, color, contrast, shape, clarity, or movement. When they appear on the screen of the device, the device performs (in real time or delayed, locally or on a remote node) an analysis of the eye movement in the video and in the speech of the subject. The video or other sensor would be able to estimate distance of the subject from the device to be used as input data for the analysis, and also measure eye movement, blurriness, or double vision, slurred speech, or incorrect or slow responses. Such measurements, individually or when analyzed together, could indicate conditions such as inebriation, delirium, or mental confusion. It even allows the presence of specific substances to be detected.

For example, the detection of nystagmus (rapid, involuntary eye movements) indicate the presence of benzodiazepines, especially if in response to the image of a cute pet lizard, the patient responds with "fierce dragon," indicating hallucinations. Or if hallucinations are detected in combination with pupil dilation the presence of Mescaline or LSD may be postulated instead.

Detecting the presence of bloodshot eyes and measuring the degree to which they are bloodshot is another potential characteristic which can be used alone in combination with other measures to further assess patient condition before or after dispensing medication.

This is discussed at:
https://americanaddictioncenters.org/health-complications-addiction/signs-drug-use-eyes The following prescription and non-prescription medicines can cause your pupils to dilate and affect their ability to react to light:
Antihistamines
Decongestants
Tricyclic antidepressants
Motion sickness medicines
Anti-nausea medicines
Anti-seizure drugs
Medications for Parkinson's disease
Botox and other medications containing botulinum toxin
Atropine (used for myopia control and other medical purposes)

In addition to eye characteristic measurements and vocal response characteristics, psychological and psychometric assessments may be performed via the device itself or on a connected device (e.g., smart phone communicating with the device via Bluetooth, WiFi, or other network.) The test can be in the form of a series of questions and responses, or in the form of required finger gestures e.g., "follow this balls around on the screen with your finger", or in the form of a game which measures reaction times, and may be self-administered or administered locally or remotely by an administrator or clinician.

Tests which measure cognitive ability cover some or all of the following categories: numerical, verbal, abstract, spatial and mechanical reasoning, perception, memory, verbal and mathematical ability, and problem solving. Such tests pose questions designed to estimate applicants' potential to use mental processes to solve work-related problems or to acquire new job knowledge.

In a simple form, a test can be a static predetermined set of questions and the user's responses assessed to detect and quantify level and rate of change of neurotoxicity, delirium and mental confusion. Tests such as these exist, and clinical studies have measured their applicability for given conditions and have quantified their level of accuracy, as discussed at: (https://www.ncbi.nlm.gov/pmc/articles/PMC1949075/)
Similar tests can also quantify cognitive impairment—see: (https://academic.oup.com/toxsci/article/58/2/222/1733952).

In the case of the present application, when results are compared against baseline tests, a change and/or rate-of-change can be measured by the device. In one embodiment, a patient may be required to take one or more such tests to create a baseline measurement before the device permits a dose to be dispensed. At a given time after dispensing (e.g., 20 minutes), the patient may be required to perform additional testing and the device could thus measure psychological and physiological responses to the dose. This may be a pre-condition for the patient to be allowed to receive a future dose. Test results which indicate presence of pathological conditions such as psychosis, mental confusion, or even allergic reaction (in response to questions such as "Do you have a rash?" or "Are you itchy?") may trigger an alert to the physician or clinic.

Examples of cognitive tests which may reliably predict neurotoxicity in humans are found at: https://academic.oup.com/toxsci/article/58/2/222/1733952
Examples of standard cognitive tests are the Wonderlic test and the Predictive Index test.

It will be appreciated that what has been described above comprises examples of systems and computer-implemented methods. One of ordinary skill in the art will recognize that other combinations and permutations of this disclosure are possible without departing from the scope and spirit of the described embodiments.

The present invention provides a unique solution, especially in the application of the blockchain for secure user authentication and near-real-time transmission of Electronic Medical Record (EMR) data, and in remote monitoring and inventory tracking and control and dispensing of any substance, especially of high-value or high-risk substances/materials.

The devices 104, 204, working in conjunction with the network 102, 202 to facilitate big data capture and analysis, thereby providing a unique solution to the opioid crisis by allowing dosages to be controlled and tapered off to allow controlled self-medication by users.

In particular, the system of the present application provides features not previously available, including:

real-time authentication to prevent abuse, dose metering to prevent overdose, real-time monitoring to provide improved oversight, statistical reporting to provide analysis and global overview, compliance reporting to protect the physician and patient, dosage tapering to avoid withdrawal symptoms and prevent addiction, geolocation to provide reliable medication location tracking and auditing, geofencing to provide law enforcement with diversion alerts and the ability to efficiently locate, arrest and recover stolen medication, a unique user identifier—e.g. thumbprint or retinal scan, or through asymmetric key encryption—to detect and prevent abuse attempts e.g., in the form of multiple simultaneous use attempts, patient medication reminders via the associated app or by communicating directly with the device and providing the device with a visual or auditory alert, physician remote monitoring capability, physician alerts if the patient misses a dose, relief of methadone patients from having to attend a clinic daily, expected decrease in MAT program drop-out rates, expected increase in MAT recovery success rates by reducing the drop-out rate, reduced recovery clinic costs by automating administration, increased recovery clinic efficiency and throughput by reducing administrative effort.

Implementation:

The device of the invention in a medical application includes a smart inhaler coupled with an onboard or external biometric sensor. In one embodiment, a physician or pharmacist connects an opioid medication cartridge into the chassis of the device and registers the patient's fingerprint and a prescription to the device. Patients take their devices with them and self-administer the medication by placing their finger on the fingerprint scanner. The controller, which is coupled to the scanner and the network, will only release the medication in accordance with the pre-programmed prescription regimen, which may be adjusted remotely by the physician, or may be adjusted automatically in the event of the detection of some form of abuse by an AI system that monitors pattern anomalies. By being able to pre-define and remotely adjust dosages, it provides the ability to deliver drugs slowly over time, further avoiding abuse or diversion, and preventing overdose.

By making use of a blockchain as the backbone to the authentication and communication of data and instructions, the system of the present invention provides another level of security to prevent abuse.

Near the end of the prescription, the device will automatically apply a physician-selected tapering schedule gradually weaning the patient from the medication naturally, thus preventing withdrawal symptoms.

Thus, instead of pills or syringes, the present invention provides a different delivery device for delivering the drug in aerosolized format, with pre-defined and/or remotely adjustable dosages and user authentication. It also generates reports to doctors, government, insurance and law enforcement.

The data capture and analysis also acts as a further safeguard against abuse by monitoring patient compliance and identifying anomalies e.g. using AI (artificial intelligence) to identify use discrepancies such as attempts to dose during non-dose periods or once a day's dose has already been delivered, or if there is an indication of missed doses.

Thus, reporting of trends is achieved through a distributed and through a central system, which also allows for the management and withdrawal of inventory. In a preferred embodiment, the Blockchain becomes the platform for inventory dispensing and big data reporting and aggregating of data from all delivery devices, whether used for drug delivery like prescription opioids or other valuable or high-risk substances.

The present application also includes interfaces in the blockchain for third party contributors (similar to Active X controls in Windows) and facilitates integration of selected data from the dispensing devices into electronic medical records (EMR) by providing EMRs with a workflow to accommodate different medical applications.

While the present application has been described with respect to specific embodiments of the delivery devices, it will be appreciated that different embodiments can be configured without departing from the invention.

What we claim is:

1. A global monitoring and authorization system, comprising a distributed network configured to receive data from multiple mobile drug delivery devices, each delivery device including a processor, memory, location sensor, communication system, and I/O interface, configured to dispense drugs, the network being operable to track the location of the delivery devices across multiple locations and monitor their use from time of prescription by physician or pharmacy through multiple dosages dispensed by the user across multiple locations, wherein drug dose, dose frequency, and at least one of user genetic, physiological and psychological reaction data to the drug is gathered in real time using sensors on or linked to the delivery devices, for research and analysis purposes to improve substance composition and substance combinations to further the development of such substances and combinations and to further substance innovation in general, and further, including artificial intelligence to identify patterns in the location data of the multiple drug delivery devices in real time across multiple locations of each drug delivery device, and identify anomalies in the location patterns of the multiple devices as they change over time, the system further including computer readable program instructions for communicating with government oversight or law enforcement agencies and providing them with reports of one or more of: the of patterns in the location data of the multiple drug delivery devices, and anomalies in the patterns.

2. The system of claim 1, wherein the system is built on a blockchain platform for secure and consensus-based validation of the movement and administration of drugs, without requiring the intervention of human arbiters.

3. The system of claim 2, wherein the blockchain is adapted to disseminate configuration information to the node devices, and store transactions.

4. The system of claim 3, wherein the transactions associated with a device include information about user interaction with the device, including one or more of user-identifying information, amount of product dispensed, time of dispensing, and geographic location of the device.

5. The system of claim 4, wherein user-identifying information serves to authenticate the user by distributed user authentication.

6. The system of claim 5, wherein distributed user authentication includes at least one of an asymmetric key encryption scheme with a public key to encrypt and a private key to decrypt the information, and consensus-based authentication involving consensus amongst a group of users.

7. The system of claim 1, wherein the drug delivery devices include secure housings to resist tampering.

8. A system for tracking and controlling mobile drug delivery devices, comprising one or more sensors on each delivery device or linked to each mobile drug delivery device for measuring physiological or psychological parameters of each user of a mobile drug delivery device in real time, and for tracking the location of the device across multiple locations, means for controlling access to the devices, and a processor associated with each device with memory encoded with logic to gather information relating to one or more of: drug delivery information, user information, and sensor data gathered by each mobile drug delivery device, wherein said logic uses the physiological or psychological sensor data to control the drug delivery, and the logic communicates the data and information to authorized parties, and wherein the logic communicates the locations of each of the mobile drug delivery devices across multiple locations in real time after the mobile drug delivery device has been prescribed to a user by a physician or pharmacy, wherein the drug delivery dose, dose frequency, and at least one of user genetic, physiological and psychological reaction data to the drug is gathered in real time using sensors on or linked to the delivery devices, for research and analysis purposes to improve substance composition and substance combinations to further the development of such substances and combinations and to further substance innovation in general, and wherein the logic includes artificial intelligence with which it identifies distribution patterns of the locations of the mobile drug delivery devices in real time and anomalies in the distribution patterns, and wherein the logic is configured to send reports to government oversight or law enforcement agencies, identifying at least one of: the distribution patterns of the delivery devices, and anomalies in the distribution patterns.

9. The system of claim 8, wherein controlling access includes protection against physical tampering with the device, and controlling dispensing of product by the device.

10. The system of claim 9, wherein control of product dispensed by the device includes at least one of, the amount and time of dispensing of product.

11. The system of claim 8, wherein communication of the data and information includes generating reports.

12. A method for reducing drug abuse, such as opioid abuse, and for addressing the problem of opioid addiction comprising, providing mobile, hack-resistant prescription-drug delivery devices;

providing a global data exchange, data gathering, and overview system of what is happening to the devices and the drugs globally, by gathering data from the hack-resistant prescription-drug delivery devices, which gathered data includes details on the dispensing of drugs by each device, and the locations of the devices in real time as the hack-resistant prescription-drug delivery devices move around across multiple locations, wherein the global data exchange, data gathering, and overview system includes sharing of dose, frequency, and at least one of user genetic, physiological and psychological reaction data to the drug and the dose and dose frequency gathered in real time using sensors on or linked to the delivery devices, for research and analysis purposes to improve substance composition and substance combinations to further the development of such substances and combinations and to further substance innovation in general, using artificial intelligence to use the locations of the devices as a whole to identify geographic distribution patterns of the devices and to identify anomalies in the distribution patterns of the devices, and sending reports to government oversight or law enforcement agencies, identifying one or more of: the geographic distribution patterns, and anomalies in the distribution patterns of the mobile devices.

13. The method of claim 12, wherein details on the dispensing of drugs includes types of drugs, and times and amounts dispensed.

14. The method of claim 13, wherein the gathered data is transmitted to government oversight or law enforcement agencies and providing them with reports for review or analysis.

15. The method of claim 12, wherein the hack-resistant prescription-drug delivery devices are configured to taper off the dosages according to a defined schedule.

16. The method of claim 15, wherein the defined schedule is user specific and is designed to-wean a user of a hack-resistant prescription-drug delivery device, off a drug, taking into account at least one of physiological and psychological information gathered on the user.

17. The method of claim 12, wherein the global data exchange, data gathering, and overview system includes authentication by consensus of a user and of requests for a dose, without human intervention.

* * * * *